United States Patent
Kurata et al.

(10) Patent No.: US 11,964,740 B2
(45) Date of Patent: Apr. 23, 2024

(54) SUBMERSIBLE SENSOR UNIT

(71) Applicant: NITTO DENKO CORPORATION, Ibaraki (JP)

(72) Inventors: Naoki Kurata, Ibaraki (JP); Tomonari Naito, Ibaraki (JP); Satoru Suzuki, Ibaraki (JP)

(73) Assignee: NITTO DENKO CORPORATION, Ibaraki (JP)

( * ) Notice: Subject to any disclaimer, the term of this patent is extended or adjusted under 35 U.S.C. 154(b) by 853 days.

(21) Appl. No.: 16/961,649

(22) PCT Filed: Jan. 15, 2019

(86) PCT No.: PCT/JP2019/000951
§ 371 (c)(1),
(2) Date: Jul. 10, 2020

(87) PCT Pub. No.: WO2019/139170
PCT Pub. Date: Jul. 18, 2019

(65) Prior Publication Data
US 2020/0339234 A1    Oct. 29, 2020

(30) Foreign Application Priority Data
Jan. 12, 2018   (JP) .................................. 2018-003181

(51) Int. Cl.
*B63B 59/04*    (2006.01)
(52) U.S. Cl.
CPC ................................. *B63B 59/045* (2013.01)
(58) Field of Classification Search
CPC ............................. B63B 59/045; B63B 59/04
See application file for complete search history.

(56) References Cited

U.S. PATENT DOCUMENTS

2013/0087042 A1   4/2013   Furuyama et al.
2015/0079345 A1   3/2015   Kurata et al.
(Continued)

FOREIGN PATENT DOCUMENTS

CN   102746969 A   10/2012
CN   103805106 A   5/2014
(Continued)

OTHER PUBLICATIONS

Office Action dated Feb. 13, 2023 for Japanese Patent Application No. 2019-565130, along with an English machine translation (13 pages).
Report of Hydrographic and Oceanographic Researches No. 51 Mar. 2014 (http://www1.kaiho.mlit.go.jp/GIJUTSUKOKUSAI/KENKYU/report/rhr51/rhr51-TR09.pdf), with an English Abstract, cited in the Specification.
(Continued)

*Primary Examiner* — Stephen P Avila
(74) *Attorney, Agent, or Firm* — Hauptman Ham, LLP

(57) ABSTRACT

As a conventional antifouling measure to prevent adherence of aquatic organisms to a submersible sensor unit, a grease containing a stimulant, such as mustard, capable of repelling aquatic organisms is applied onto a sensing part thereof, thereby preventing adherence of the aquatic organisms. However, the irritant-containing grease applied onto the sensing part will come off within one to two months, resulting in disappearance of its effect. Thus, it is necessary to perform work of pulling up the submersible sensor unit and re-applying the grease, in each case. The present invention provides a water flow resistant submersible sensor unit which comprises an aquatic organism adherence preventive film capable of preventing adherence of aquatic organisms even when used in the submersible sensor unit for about half a year, almost without involving any underwater movement, and capable of, after use, being easily peeled off from the submersible sensor unit.

9 Claims, 5 Drawing Sheets

(56) References Cited

U.S. PATENT DOCUMENTS

2015/0246319 A1 9/2015 Furuyama et al.
2018/0079934 A1 3/2018 Suzuki et al.

FOREIGN PATENT DOCUMENTS

| CN | 106716603 A | 5/2017 |
| EP | 2 583 734 A1 | 4/2013 |
| JP | S62-86797 U | 6/1987 |
| JP | H1-104563 U | 7/1989 |
| JP | 2012-20280 A | 2/2012 |
| JP | 2015-174902 A | 10/2015 |
| JP | 2016-108416 A | 6/2016 |
| JP | 6219551 B2 | 10/2017 |
| KR | 10-2013-0061466 A | 6/2013 |
| KR | 10-2013-0098728 A | 9/2013 |
| WO | 01/60923 A1 | 8/2001 |
| WO | 01/81474 A1 | 11/2001 |

OTHER PUBLICATIONS

International Search Report issued for corresponding International Patent Application No. PCT/JP2019/000951 dated Mar. 12, 2019, along with an English translation, citing above-references.

Written Opinion issued for corresponding International Patent Application No. PCT/JP2019/000951 dated Mar. 12, 2019, citing above-references.

Official Action dated Jun. 10, 2022, for European Patent Application No. 19 738 905.9.

The Extended European Search Report issued for corresponding European Patent Application No. 19738905.9 dated Oct. 21, 2021.

Office Action dated Sep. 21, 2022 for corresponding Chinese Patent Application No. 201980007997.4, along with an English translation (17 pages).

Office Action dated Jan. 29, 2022 for corresponding Chinese Patent Application No. 201980007997.4, along with an English machine translation.

Office Action dated Jul. 29, 2023, for corresponding Chinese patent application No. 201980007997.4, along with an English translation (17 pages).

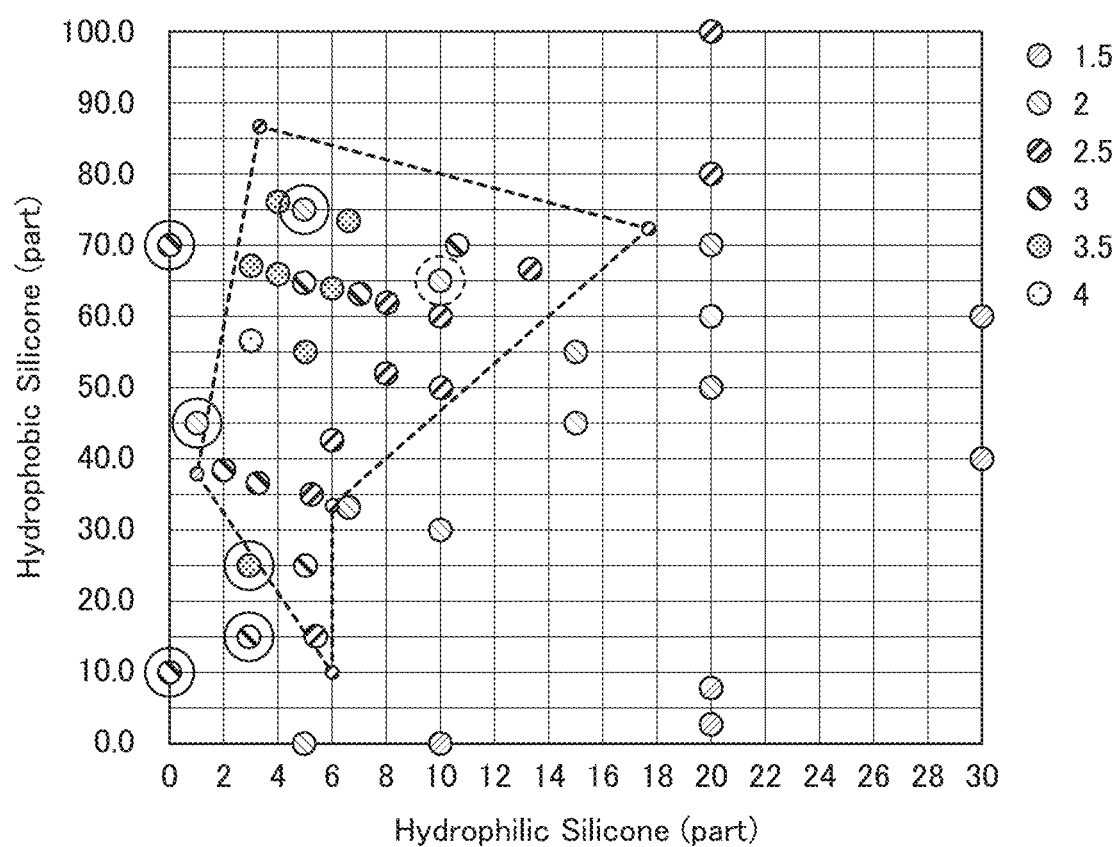

SUBMERSIBLE SENSOR UNIT

CROSS REFERENCE TO RELATED APPLICATION

This application is a National Stage of International Application No. PCT/JP2019/000951, filed on Jan. 15, 2019, which designates the United States and was published in Japan, and which claims priority to Japanese Patent Application No. 2018-003181, filed on Jan. 12, 2018 in the Japan Patent Office. Both of the aforementioned applications are hereby incorporated by reference in their entireties.

TECHNICAL FIELD

The present invention relates to a submersible sensor unit in which a sensing part is provided with a film for preventing adherence of aquatic organisms. More particularly, the present invention relates to a submersible sensor unit capable of preventing adherence of marine organisms over a long period of time so as to avoid impediment to its sensing function, and suitable for marine surveys.

BACKGROUND ART

A submersible sensor to be used for marine surveys includes sensors utilizing acoustic properties of ultrasonic waves or the like (a bathometer, a flow velocity meter, an underwater sonic velocity meter, a seabed-mounted wave height meter, a fishfinder, a seabed topography sensor, a sonar, etc.), and sensors utilizing optical properties of visible light or the light (a turbidity meter, a chlorophyll meter, an ultraviolet (UV) meter, an underwater camera, etc.), a suitable one of which is used depending on the intended purpose of a marine survey and use conditions. Among them, an acoustic Doppler current profiler (ADCP) is one non-contact flow velocity meter for measuring the flow volume and velocity of oceanic current, tidal current, river current or the like, by utilizing the Doppler effect of ultrasonic waves. For example, when the ADCP is used for a survey intended to observe the flow volume, flow velocity or the like of ocean current in a specific sea area, the ADCP is equipped in, e.g., a drifting buoy for performing observation while drifting on the sea surface, or an anchored buoy which is fixed to the seabed via an anchor, and used as a submersible sensor unit. Further, the turbidity meter configured to optically perform measurement can also be used as a submersible sensor unit.

The above submersible sensor unit equipped in a buoy is mainly used for fixed-point observation, and thus the flow of water hitting this submersible sensor unit is not so strong, differently from another type of submersible sensor unit equipped in a boat/ship to perform observation while moving. Therefore, if the fixed-point observation is performed for a long period of time in a state in which aquatic organisms adhering to the submersible sensor unit are not swept away, a large amount of aquatic organisms adhere to the submersible sensor unit and propagate to cover a sensing part thereof configured to emit an ultrasonic wave or light therefrom, leading to a problem of impeding a sensing function based on the ultrasonic wave or light. For example, barnacles, seaweeds or the like adhere to the submersible sensor unit used for a marine survey, and propagate to cover the sensing part, causing a problem that the sensing part fails to function. As one example, an organism having a hard shell, such as a barnacle, exerts a bad influence on sonic properties, e.g., it causes an increase in a difference in acoustic impedance from seawater, and thereby a sonic wave is more likely to be reflected or attenuated.

As a conventional antifouling measure to prevent adherence of aquatic organisms to the submersible sensor unit, a grease containing an irritant, such as mustard, capable of repelling aquatic organisms is applied onto the sensing part, thereby preventing adherence of the aquatic organisms (see the following Non-Patent Document 1).

CITATION LIST

Non-Patent Document

Non-Patent Document 1: Report of Hydrographic and Oceanographic Researches No. 51 March, 2014 (http://wwwl.kaiho.mlit.go.jp/GUUTSUKOKUSAI/KENKYU/report/rhr51/rhr51-TR09.pdf)

SUMMARY OF INVENTION

Technical Problem

However, the irritant-containing grease applied onto the sensing part will come off within one to two months, resulting in disappearance of its effect. Thus, it is necessary to perform work of pulling up the submersible sensor unit and re-applying the grease, in each case. Alternatively, an antifouling paint to be used for boats/ships can be applied to the sensing part to prevent adherence of aquatic organisms. In this case, however, during peeling off a film of the paint, the surface of the sensing part is likely to be damaged due to peel-off thereof together with the paint film. This damage is undesirable because it exerts an influence on sensing accuracy of the sensor.

It is therefore a primary object of the present invention to provide a water flow resistant submersible sensor unit which comprises an aquatic organism adherence preventive film capable of preventing adherence of aquatic organisms even when used in the submersible sensor unit for about half a year, almost without involving any underwater movement, and capable of, after use, being easily peeled off from the submersible sensor unit.

Solution to Technical Problem

In order to achieve the above problems, according to one aspect of the present invention, there is provided a submersible sensor unit which comprises: a housing having at least one sensing opening; a sensor disposed inside the housing such that a sensing face thereof faces the sensing opening of the housing; and an aquatic organism adherence preventive film attached to the housing or the sensing face such that it closes up the sensing opening of the housing, wherein the aquatic organism adherence preventive film has transmissibility with respect to at least one of light and a sonic wave, and wherein the aquatic organism adherence preventive film is a laminate comprising: a substrate layer; a pressure-sensitive adhesive layer bonded to one surface of the substrate layer; and an antifouling layer bonded to the substrate layer on a side opposite to the pressure-sensitive adhesive layer.

Preferably, in the submersible sensor unit of the present invention, the antifouling layer has a water contact angle of 80 degrees or less, as measured after 5 minutes have elapsed since operation of causing the antifouling layer to be in contact with methanol for 20 minutes, and then dropping water on the antifouling layer.

Preferably, in the submersible sensor unit of the present invention, a ratio of a tensile breaking strength (N/20 mm) as measured after immersion in pure water at 60° C. for 4 days to an adhesive force (N/20 mm) with respect to the submersible sensor unit, as measured after immersion in pure water at 60° C. for 4 days, is 1.5 or more.

Preferably, in the submersible sensor unit of the present invention, a 1-mm square cross-cut stretching-caused peeling degree of the antifouling layer with respect to the substrate layer is 0.30 or less.

Preferably, in the submersible sensor unit of the present invention, an amount of attenuation of a 1 MHz ultrasonic wave due to the aquatic organism adherence preventive film is 5.0 db or less.

Preferably, in the submersible sensor unit of the present invention, the aquatic organism adherence preventive film has a transmittance in a wavelength range of 400 to 800 nm of 80% or more.

Preferably, in the submersible sensor unit of the present invention, the antifouling layer contains a silicone resin and silicone oil.

Preferably, in the submersible sensor unit of the present invention, the antifouling layer has a thickness of 10 μm to 1000 μm.

Preferably, in the submersible sensor unit of the present invention, the substrate layer comprises a polyethylene-based ionomer substrate.

Preferably, in the submersible sensor unit of the present invention, the substrate layer has a thickness of 10 μm to 1000 μm.

Preferably, in the submersible sensor unit of the present invention, the pressure-sensitive adhesive layer has a thickness of 1 μm to 1000 μm.

Effect of Invention

The present invention can almost prevent adherence of aquatic organisms by the antifouling layer on the surface of the aquatic organism adherence preventive film, thereby reducing the risk of failing to perform data acquisition by a sensing function of a sensing part.

BRIEF DESCRIPTION OF DRAWINGS

FIG. 7 is a plot diagram showing a relationship among, the amount of addition (parts) of hydrophilic silicone oil contained in the aquatic organism adherence preventive film, the addition amount (weight part(s)) of hydrophobic silicone oil contained in the aquatic organism adherence preventive film, and a stretch ratio at peel-off of the antifouling layer.

DESCRIPTION OF EMBODIMENTS

Figure 1:
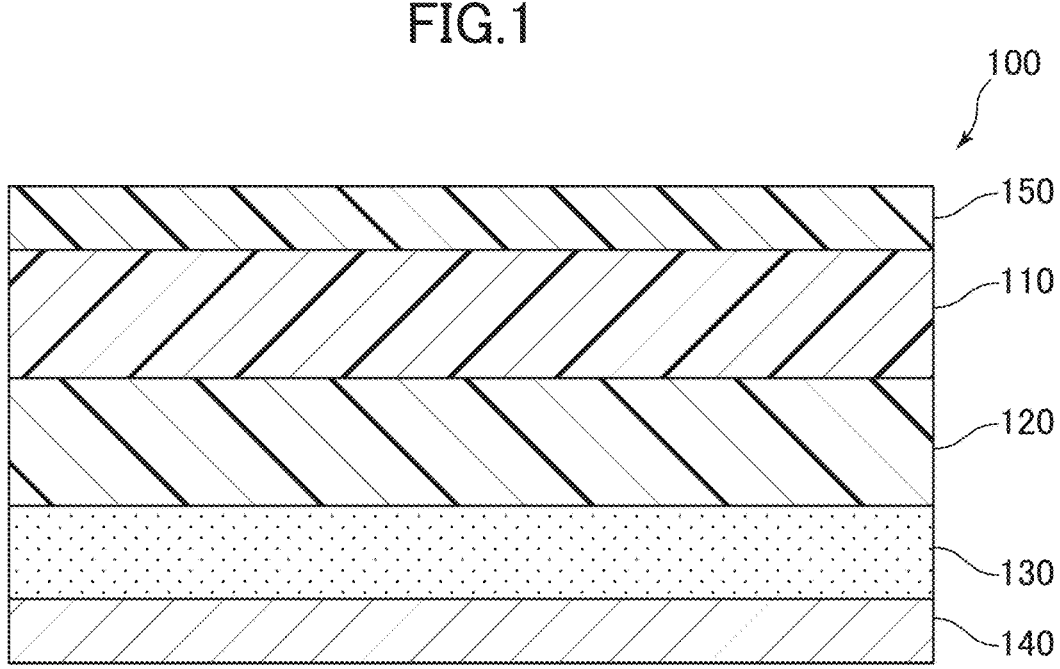
FIG. 1 is a sectional view of a laminate composing an aquatic organism adherence preventive film.
Figure 2:
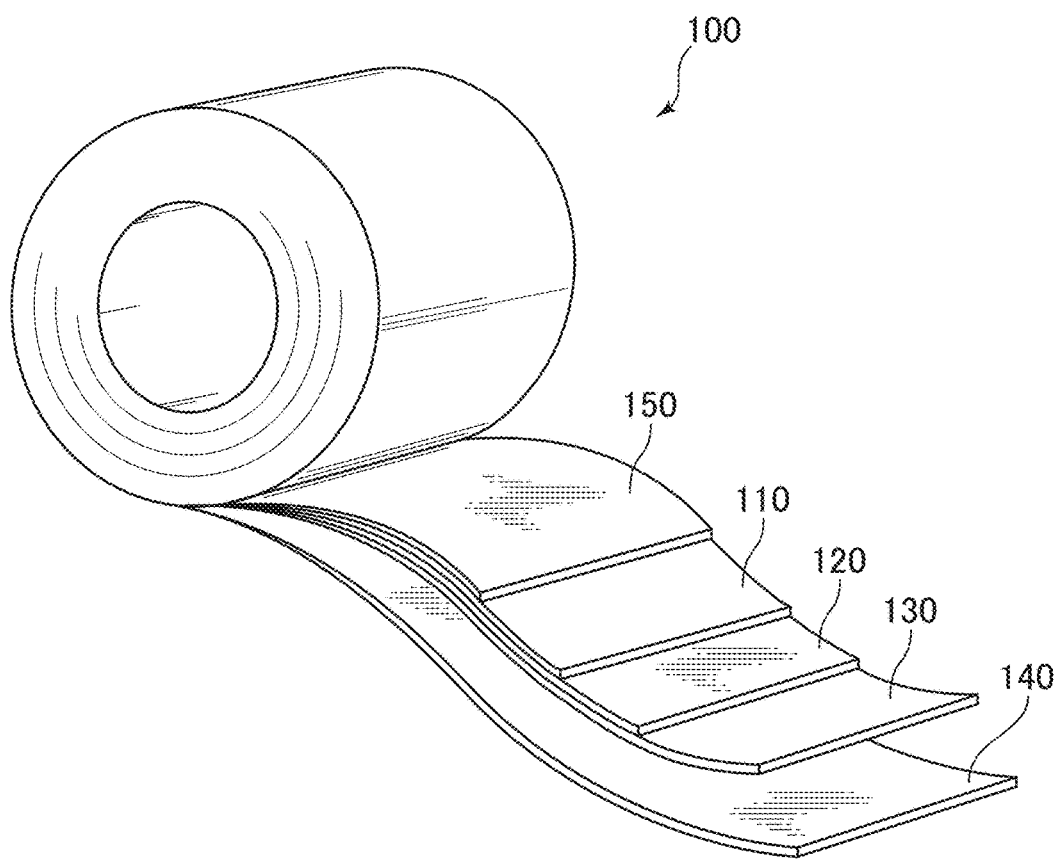
FIG. 2 is a diagram showing the external appearance of the aquatic organism adherence preventive film in the form of tape.

With reference to the drawings, an embodiment of the present invention will now be described. FIG. 1 is a sectional view of a laminate composing an aquatic organism adherence preventive film. FIG. 2 is a diagram showing the external appearance of the aquatic organism adherence preventive film in the form of tape. The aquatic organism adherence preventive film 100 is a laminate comprising a substrate layer 120, a pressure-sensitive adhesive layer 130 bonded to one surface of the substrate layer 120, and an antifouling layer 110 bonded to the substrate layer 120 on the side opposite to the pressure-sensitive adhesive layer 130. Additionally, a release liner 140 is releasably bonded to the pressure-sensitive adhesive layer 130 on the side opposite to the substrate layer 120. Further, a protective layer 150 is releasably bonded to the antifouling layer 110 on the side opposite to the substrate layer 120.

When using the aquatic organism adherence preventive film 100, the release liner 140 is peeled off from the pressure-sensitive adhesive layer 130 to allow the aquatic organism adherence preventive film 100 to be attached to an underwater structure or the like through the exposed pressure-sensitive adhesive layer 130, and the protective layer 150 is peeled off from the antifouling layer 110 so as to prevent adherence of aquatic organisms by the exposed antifouling layer 110.

Generally, when applying the aquatic organism adherence preventive film to a boat/ship or the like, even if aquatic organisms adhere to the antifouling layer, the aquatic organisms can be peeled off to some extent by water flow arising from movement of the boat/ship or the like. On the other hand, when applying the aquatic organism adherence preventive film to a sensor unit equipped in a buoy floating on the sea surface, such peel-off cannot be expected, because the buoy merely drifts with ocean current without moving by itself, and thereby a water flow hitting the sensor unit is weak. Therefore, as a design for preventing adherence of aquatic organisms, the aquatic organism adherence preventive film 100 according to this embodiment comprises the antifouling layer 110 whose surface is hydrophilized by hydrophilic silicone oil (hereinafter referred to simply as "hydrophilic oil"), Preferably, the antifouling layer 110 contains a silicone resin. The content rate of the silicone resin in the antifouling layer 110 is preferably from 30 weight % to 90 weight %, more preferably from 40 weight % to 85 weight %, further preferably from 45 weight % to 80 weight %. Since the content rate of the silicone resin in the antifouling layer falls within the above range, it is possible to more sufficiently develop an antifouling effect of the antifouling layer, and more sufficiently develop mechanical properties of the antifouling layer. The silicone resin may be a condensed-type silicone resin, or may be an addition-type silicone resin.

Preferably, the antifouling layer 110 further contains silicone oil. The content of the silicone oil with respect to 100 weight parts of the silicone resin is preferably from 20 weight parts to 150 weight parts, more preferably from 30 weight parts to 140 weight parts, further preferably from 50 weight parts to 130 weight parts.

As the silicone oil, it is possible to use: dimethyl silicone oil in which all groups are methyl groups; methylphenyl silicone oil obtained by substituting a part of the methyl groups of the dimethyl silicone oil with a phenyl group; amino-modified silicone oil obtained by substituting a part of the methyl groups of the dimethyl silicone oil with a monoamine, diamine or aminopolyether group; epoxy-modified silicone oil obtained by substituting a part of the methyl groups of the dimethyl silicone oil with an epoxy, alicyclic epoxy, epoxy polyether or epoxy aralkyl group; carbinol-modified silicone oil obtained by substituting a part of the methyl groups of the dimethyl silicone oil with a carbinol group; mercapto-modified silicone oil obtained by substituting a part of the methyl groups of the dimethyl silicone oil with a mercapto group; carboxyl-modified silicone oil obtained by substituting a part of the methyl groups of the dimethyl silicone oil with a carboxyl group; methacryl-modified silicone oil obtained by substituting a part of the methyl groups of the dimethyl silicone oil with a methacryl group; polyether-modified silicone oil obtained by substituting a part of the methyl groups of the dimethyl silicone oil with a polyether group; long-chain alkyl-modified silicone oil obtained by substituting a part of the methyl groups of the dimethyl silicone oil with a long-chain alkyl or alkyl aralkyl group; higher fatty acid-modified silicone oil obtained by substituting a part of the methyl groups of the dimethyl silicone oil with a higher fatty acid ester group; or fluoroalkyl-modified silicone oil obtained by substituting a part of the methyl groups of the dimethyl silicone oil with a fluoroalkyl group. Further, the methylphenyl silicone oil, the polyether-modified silicone oil, or the long-chain alkyl-modified silicone oil may be used. Further, from a viewpoint of adhesion, the methylphenyl silicone oil, the polyether-modified silicone oil, or the long-chain alkyl-modified silicone oil may also be used. The above silicone oils may be used independently or in combination of two or more of them. Preferably, the polyether-modified silicone oil comprises a PEG chain having an alkyl group, at a terminal thereof, wherein more preferably, the alkyl group is a methyl group.

As one practical example, the antifouling layer 110 may comprise an addition-type silicone resin, hydrophobic silicone oil, and hydrophilic oil. Here, the term "hydrophilic oil" means oil having a hydrophilic functional group. In another practical example, condensed-type silicone oil may be used instead of the addition-type silicone resin. As the hydrophobic silicone oil (hereinafter referred to simply as "hydrophobic oil"), it is possible to use, e.g., dimethyl silicone oil, and alkyl-modified silicone oil, and, as the hydrophilic oil, it is possible to use, e.g., polyether-modified silicone oil, and carbinol-modified silicone oil.

Although the thickness of the antifouling layer 110 is not particularly limited, it is preferably from 10 to 1000 μm, more preferably from 20 to 500 μm, further preferably from 30 to 300 μm, particularly preferably from 50 to 200 μm.

The substrate layer may be comprised of, e.g., a polyurethane resin, a polyurethane acrylic resin, a rubber-based resin, a polyvinyl chloride resin, a polyvinyl acetate resin, a polyester resin, a silicone resin, a fluorine resin, a polyamide resin, a polyolefin resin (polyethylene, polypropylene, etc.), or an ionomer resin. The ionomer resin is an ionic polymer comprising a hydrophobic polymer main chain, and an ionic group of a metal or ammonium salt of a carboxylic acid, a sulfonic acid or the like partially included as a side chain in a small amount, and is a resin having an ionic cross-linking in the molecule As one practical example, the substrate layer 120 may be comprised of a polyethylene-based ionomer. Although the thickness of the substrate layer 120 is not particularly limited, it is preferably from 10 to 1000 μm, more preferably from 20 to 500 μm, further preferably from 30 to 400 μm, particularly preferably from 50 to 300 μm.

Examples of the pressure-sensitive adhesive layer 130 include an acrylic resin-based pressure-sensitive adhesive, an epoxy resin-based pressure-sensitive adhesive, an amino resin-based pressure-sensitive adhesive, a vinyl resin-based (e.g., vinyl acetate-based polymer) pressure-sensitive adhesive, a curable acrylic resin-based pressure-sensitive adhesive, and a silicone resin-based pressure-sensitive adhesive. As one practical example, the pressure-sensitive adhesive layer 130 may be an acrylic resin-based pressure-sensitive adhesive composing an acrylic polymer or the like. For example, the acrylic polymer is obtained by polymerizing a monomer composition consisting mainly of (meth)acrylic acid ester. As used therein, the term "(meth)acryl" in "(meth)acrylic acid" or the like means "acryl and/or methacryl".

Examples of the (meth)acrylic acid ester include methyl (meth)acrylate, ethyl (meth)acrylate, propyl (meth)acrylate, isopropyl (meth)acrylate, butyl (meth)acrylate, isobutyl (meth)acrylate, sec-butyl (meth)acrylate, t-butyl (meth)acrylate, pentyl (meth)acrylate, neopentyl (meth)acrylate, isoamyl (meth)acrylate, hexyl (meth)acrylate, heptyl (meth)acrylate, octyl (meth)acrylate, 2-ethylhexyl (meth)acrylate, isooctyl (meth)acrylate, nonyl (meth)acrylate, isononyl (meth)acrylate, decyl (meth)acrylate, isodecyl (meth)acrylate, undecyl (meth)acrylate, dodecyl (meth)acrylate, tridecyl (meth)acrylate, tetradecyl (meth)acrylate, pentadecyl (meth)acrylate, hexadecyl (meth)acrylate, heptadecyl (meth)acrylate, and octadecyl (meth)acrylate. These alkyl (meth)acrylic acid esters may be used independently or in combination of two or more of them.

The monomer composition may further comprise: a carboxyl group-containing monomer such as (meth)acrylic acid; a hydroxyl group-containing monomer such as 2-hydroxybutyl (meth)acrylate; and a cyclic nitrogen-containing monomer such as N-vinyl pyrrolidone or N-vinyl-ε-caprolactam.

Although the thickness of the pressure-sensitive adhesive layer 130 is not particularly limited, it is preferably from 1 to 1000 μm, more preferably from 5 to 500 μm, further preferably from 10 to 400 μm, particularly preferably from 20 to 300 μm.

With regard to each of the antifouling layer 110, the substrate layer 120 and the pressure-sensitive adhesive layer 130 of the aquatic organism adherence preventive film 100, the composition and others thereof will be described in detail in the aftermentioned Examples.

With regard to the antifouling layer 110 on the substrate layer 120, it is considered that a layer of hydrophobic silicone oil is formed on one surface thereof on the side opposite to the other surface in contact with the substrate layer 120, wherein a layer of hydrophilic silicone oil is formed on the layer of hydrophobic silicone oil, and a hydration layer is formed on the layer of hydrophilic silicone oil. Further, the hydration layer is presumed to serve as the surface of the antifouling layer 110 to prevent adherence of aquatic organisms such as barnacles and seaweeds.

Figure 3:
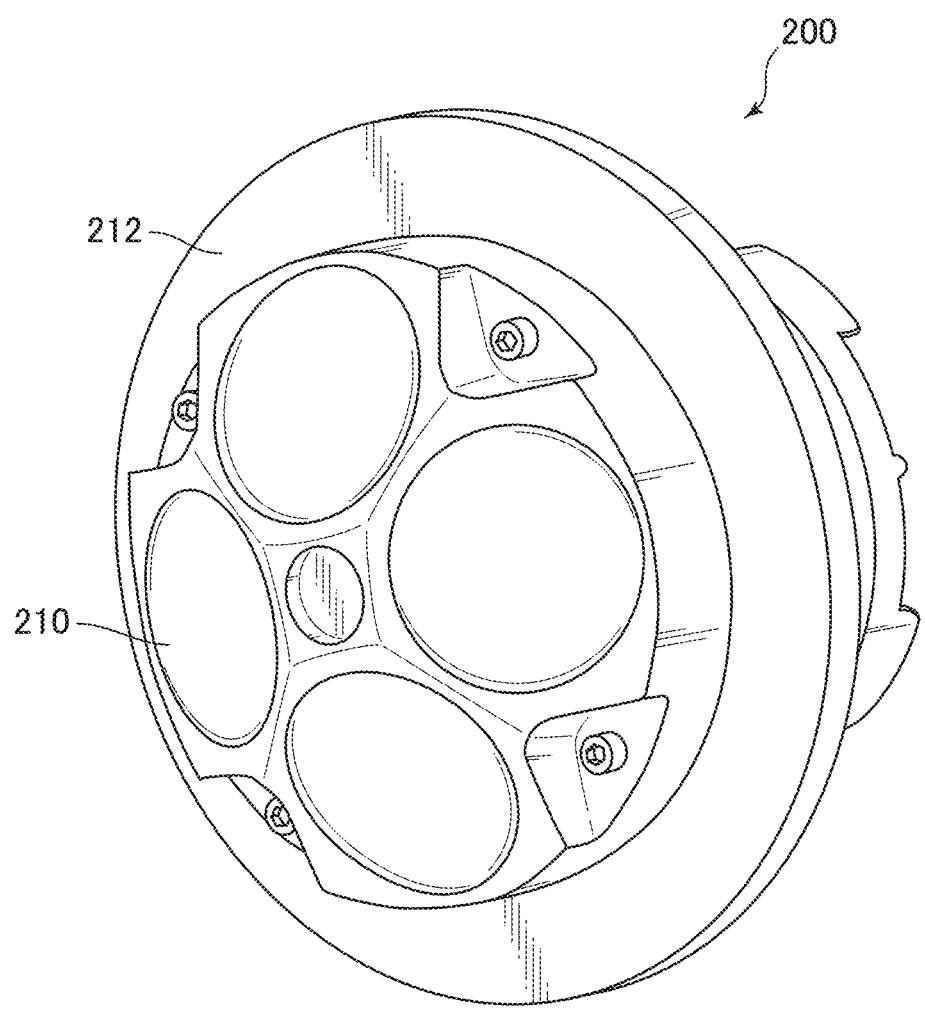
FIG. 3 is a diagram showing the external appearance of a submersible sensor unit according to one embodiment of the present invention.

FIG. 3 is a diagram showing the external appearance of a submersible sensor unit according to one embodiment of the present invention. The submersible sensor unit 200 is one type of multi-layer flow direction/velocity meter, called "acoustic Doppler current profiler (ADCP)". The submersible sensor unit 200 comprises a housing having at least one sensing opening. The submersible sensor unit 200 also comprises a sensor 210 disposed inside the housing such that a sensing face thereof faces the sensing opening of the housing. A mounting member 212 protruding in flange form from the housing of the submersible sensor unit 200 can be used for fixing the submersible sensor unit 200 to a buoy or a boat/ship.

Figure 4:
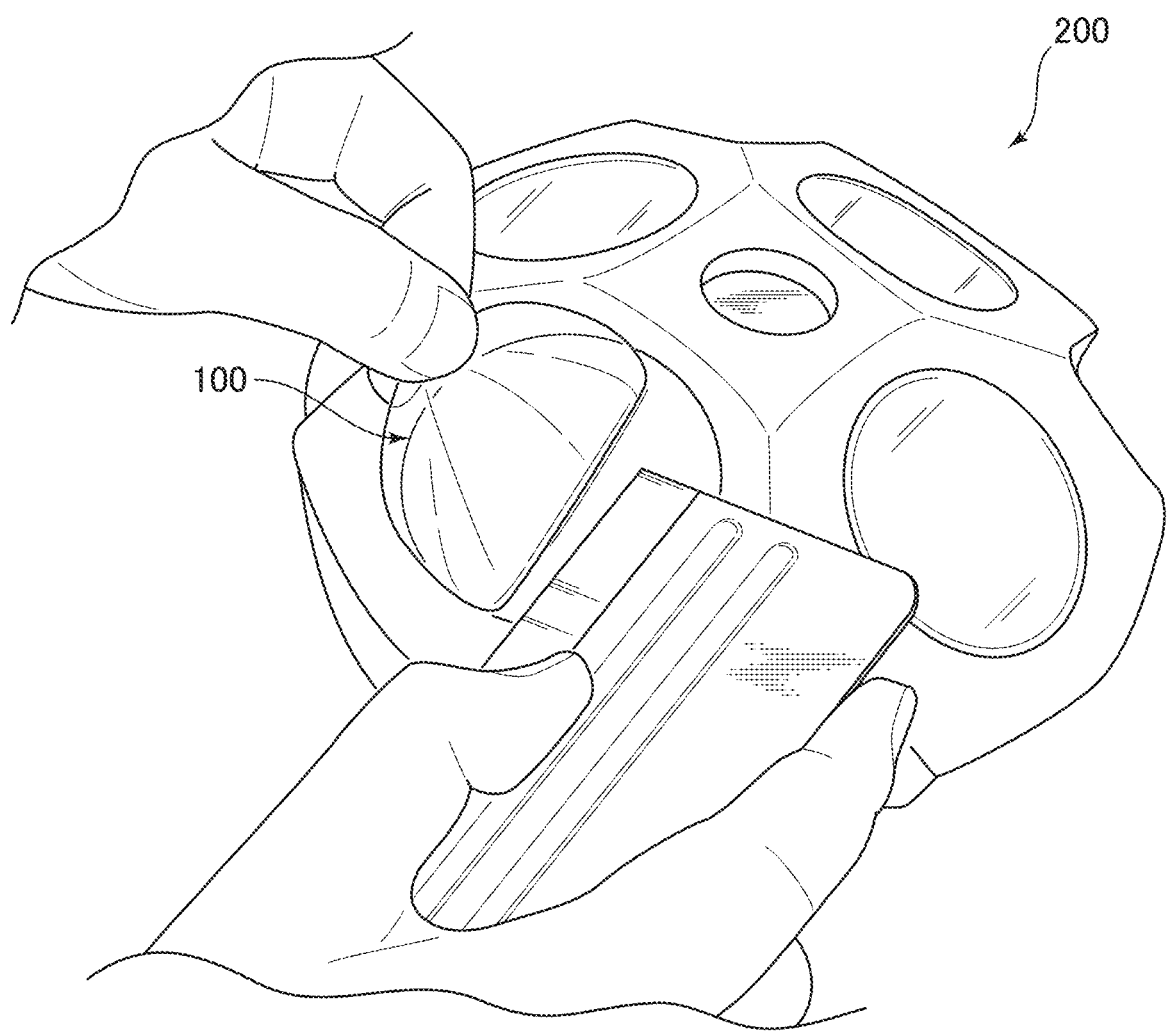
FIG. 4 is a diagram showing the state of work of attaching the aquatic organism adherence preventive film to the submersible sensor unit.

FIG. 4 is a diagram showing the state of work of attaching the aquatic organism adherence preventive film to the submersible sensor unit. The aquatic organism adherence preventive film 100 is attached to a sensing face of the sensor 200 or the housing of the submersible sensor unit 200, such that it closes the sensing opening of the housing of the submersible sensor unit 200. The attachment of the aquatic organism adherence preventive film 100 can be performed using a jig or the like. The aquatic organism adherence preventive film 100 has transmissibility (permeability) with respect to at least one of light and a sonic wave.

When measuring attenuation of an ultrasonic wave occurring in a situation where an antifouling measure is taken against the sensing part of the ADCP as one type of submersible sensor unit, the amount of the attenuation by an antifouling measure based on the aquatic organism adherence preventive film was equivalent to or equal to or less than that that by the conventional antifouling measure configured to apply a grease containing a stimulant such as mustard.

(Measurement of Ultrasonic Wave Attenuation Amount)

The measurement of attenuation of an ultrasonic wave is performed by a two-probe method in the following manner. A 6-L plastic container (20 cm×30 cm×10 cm depth) was filled with pure water at room temperature (23° C.). Then, after putting therein an ultrasonic concentration meter (AM1S-10S-1A (measurement frequency: 1 MHz) manufactured by Ultrasonic Engineering Co., Ltd., sensor pitch: 100 mm), the container was left untouched for 30 minutes or more to reduce temperature variation. A zero point adjustment was performed by a converter (AE4 (UAM-4MK2) manufactured by Ultrasonic Engineering Co., Ltd.), such that the attenuation amount becomes 0 db in a state before attaching a sample. A sample was cut into a circular shape having a diameter of 30 mm. Then, the sample (film, grease) was pressed against and attached to a sonic wave transmitting and receiving part in water, while avoiding taking in an air bubble. When an air bubble or the like adheres to the surface of the sample, it was removed by a brush. After the elapse of 120 seconds since the attachment of the sample, the attenuation amount (db) at 1 MHz=20×Log (P/PO) was measured, where P denotes a received sound pressure intensity in the presence of the sample, and P0 denotes a received sound pressure intensity in the absence of the sample.

In the conventional antifouling measure, a grease containing a stimulant such as mustard is applied onto a sensing part of the ADCP as one type of submersible sensor unit, thereby preventing adherence of aquatic organisms. Firstly, attenuation of an ultrasonic wave (1 MHz) was measured under the condition that a grease was applied onto a sensing part of the ultrasonic concentration meter, while the thickness of the applied grease was set to 5 mm, 6 mm and 7 mm. As a result, the attenuation amount was 2.5 db, 3.0 db, and 6.1 db, respectively. On the other hand, attenuation of the ultrasonic wave was measured under the condition that a conventional aquatic organism adherence preventive film (e.g., the film described in the Patent Document 1) was attached to the sensing part of the ultrasonic concentration meter. As a result, the attenuation amount was 2.7 db. In the conventional antifouling measure, if the thickness of the grease is increased in view of a long-term operation of the submersible sensor unit, it undesirably influences transmission of an ultrasonic wave, leasing to an increase in the attenuation amount, as compared to an antifouling measure based on an aquatic organism adherence preventive film. Thus, the conventional antifouling measure is not suited to the long-term operation of the submersible sensor unit.

The amount of attenuation of a 1 MHz ultrasonic wave due the aquatic organism adherence preventive film pertaining to the present invention is preferably 5.0 db or less, more preferably 4.5 db or less, particularly preferably 4.0 db or less. Further, from a viewpoint of facilitating visual check of the presence or absence of an air bubble on an attachment surface during attachment, a transmissivity of the aquatic organism adherence preventive film pertaining to the present invention, with respect to visible light having a wavelength rage of 400 to 800 nm is preferably 80% or more, more preferably 85% or more, particularly preferably 90% or more. Considering that an air bubble on the attachment surface leads to deterioration in the sensitivity of the sensor and deterioration in adhesion, it is preferable to attain a situation where there is no air bubble.

EXAMPLES

The present invention will now be described in detail based on examples of an antifouling layer-including pressure-sensitive adhesive film (aquatic organism adherence preventive film). However, it should be noted that the present invention is not limited to the following examples, as long as it does not depart from the spirit and scope thereof as set forth in appended claims. A list of Inventive Examples and Reference Examples is shown in Table 1.

TABLE 1

| | Composition of Antifouling Layer (weight part) | | | | | | | | |
|---|---|---|---|---|---|---|---|---|---|
| | Silicone Resin | | | | | | | | |
| | KE-1935 (Addition Type) | KE-1950 (Addition Type) | KE-445 (Condensed Type) | Hydrophobic Silicone Oil | | | hydrophilic Silicone Oil | | |
| | | | | KF96-100cs | KF415 | KF50-100cs | KF6013 | KF6015 | KF6016 |
| Inventive Example 1 | 100 | | | 35 | 20 | | | 10 | 5 |
| Inventive Example 2 | 100 | | | 45 | 20 | | | 10 | |
| Inventive Example 3 | 100 | | | 40 | 20 | | 10 | | |
| Inventive Example 4 | 100 | | | 40 | 20 | | | | |
| Inventive Example 5 | 100 | | | 65 | | | | | 5 |

TABLE 1-continued

| | | | | | | |
|---|---|---|---|---|---|---|
| Inventive Example 6 | 100 | | 35 | 8 | 4 | 2 |
| Inventive Example 7 | 100 | | 35 | 20 | 10 | 5 |
| Inventive Example 8 | 100 | | 35 | 20 | 10 | 5 |
| Inventive Example 9 | 100 | | 35 | 20 | 10 | 5 |
| Inventive Example 10 | 100 | | 35 | 20 | 10 | 5 |
| Inventive Example 11 | 100 | | 35 | 20 | 10 | 5 |
| Inventive Example 12 | 100 | | 35 | 20 | 10 | 5 |
| Inventive Example 13 | 100 | | 35 | 20 | 10 | 5 |
| Inventive Example 14 | 100 | | 35 | 20 | 10 | 5 |
| Inventive Example 15 | 100 | | 35 | 20 | 10 | 5 |
| Inventive Example 16 | 100 | | 35 | 20 | 10 | 5 |
| Inventive Example 17 | 100 | | 35 | 20 | 10 | 5 |
| Inventive Example 18 | | 100 | 65 | | | 5 |
| Reference Example 1 | 100 | | 70 | | | |
| Reference Example 2 | 100 | | 26 | 20 | | 1 |
| Reference Example 3 | 100 | | 35 | 20 | 10 | 5 |
| Reference Example 4 | 100 | | 35 | 20 | 10 | 5 |
| Reference Example 5 | | 100 | | | 10 | |
| Reference Example 6 | | 100 | 60 | | | |
| Reference Example 7 | | 100 | 75 | | | |
| Reference Example 8 | | 100 | 70 | | | |

| | Composition of Antifouling Layer (weight part) | | | Substrate | | Pressure-Sensitive Adhesive | |
|---|---|---|---|---|---|---|---|
| | | Others | | | | | |
| | hydrophilic Silicone Oil KF6017 | Liquid Paraffin | Thickness μm | Type | Thickness μm | Composition | Thickness μm |
| Inventive Example 1 | | | 100 | Ionomer | 100 | 2EHA/NVP | 50 |
| Inventive Example 2 | | | 100 | Ionomer | 100 | 2EHA/NVP | 50 |
| Inventive Example 3 | | | 100 | Ionomer | 100 | 2EHA/NVP | 50 |
| Inventive Example 4 | 10 | | 100 | Ionomer | 100 | 2EHA/NVP | 50 |
| Inventive Example 5 | | | 100 | Ionomer | 100 | 2EHA/NVP | 50 |
| Inventive Example 6 | | | 100 | Ionomer | 100 | 2EHA/NVP | 50 |
| Inventive Example 7 | | | 50 | Ionomer | 100 | 2EHA/NVP | 50 |
| Inventive Example 8 | | | 200 | Ionomer | 100 | 2EHA/NVP | 50 |
| Inventive Example 9 | | | 100 | Ionomer | 100 | 2EHA/NVP | 20 |
| Inventive Example 10 | | | 100 | Ionomer | 100 | 2EHA/NVP | 300 |
| Inventive Example 11 | | | 100 | Ionomer | 50 | 2EHA/NVP | 50 |
| Inventive Example 12 | | | 100 | Ionomer | 300 | 2EHA/NVP | 50 |
| Inventive Example 13 | | | 100 | PVC/PVAc with primer | 30 | 2EHA/NVP | 50 |
| Inventive Example 14 | | | 100 | PVC with primer | 100 | 2EHA/NVP | 50 |
| Inventive Example 15 | | | 100 | PET with primer | 38 | 2EHA/NVP | 50 |

TABLE 1-continued

| | | | | | | |
|---|---|---|---|---|---|---|
| Inventive Example 16 | | | 100 | Urethane with primer | 100 | 2EHA/NVP | 50 |
| Inventive Example 17 | | | 100 | Urethane with primer | 100 | 2EHA/AA | 50 |
| Inventive Example 18 | | | 100 | Ionomer | 100 | 2EHA/NVP | 50 |
| Reference Example 1 | | | 100 | Ionomer | 100 | 2EHA/NVP | 50 |
| Reference Example 2 | | | 100 | Ionomer | 100 | 2EHA/NVP | 50 |
| Reference Example 3 | | | 100 | Urethane | 100 | 2EHA/NVP | 50 |
| Reference Example 4 | | | 100 | PVC/PVAc with primer | 18 | 2EHA/NVP | 50 |
| Reference Example 5 | | | 150 | Urethane Acrylic | 150 | 2EHA/NVP | 50 |
| Reference Example 6 | 30 | 5 | 100 | Urethane | 100 | 2EHA/AA | 50 |
| Reference Example 7 | 5 | 5 | 100 | Urethane | 100 | 2EHA/AA | 50 |
| Reference Example 8 | 20 | | 100 | Ionomer | 100 | 2EHA/AA | 50 |

Production Example 1

100 weight parts of toluene, 60 weight parts of dicyclopentanyl methacrylate (trade name "FA-513M", manufactured by Hitachi Chemical Co., Ltd.), 40 weight parts of methyl methacrylate, and 3 weight parts of thioglycollate as a chain transfer agent were put into a four-necked flask as a reaction vessel equipped with a cooling tube, a nitrogen inlet tube, a thermometer, and a stirring device. Subsequently, the resulting mixture was stirred under a nitrogen atmosphere at 70° C. for 1 hour, and then 0.2 weight part of azobisisobutyronitrile as a thermal polymerization initiator was put therein. The resulting mixture was subjected to a reaction at 70° C. for 2 hours, and then to a reaction at 80° C. for 2 hours. Subsequently, the resulting reacted liquid was put into and dried by an atmosphere at a temperature of 130° C. to remove toluene, the chain transfer agent, and unreacted monomers, thereby obtaining a solid acrylic polymer.

Inventive Example 1

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 35 weight parts of dimethyl silicone oil (trade name "KF96-100 cs", manufactured by Shin-Etsu Chemical Co. Ltd.), 20 weight parts of alkyl-modified silicone oil (trade name "KF415", manufactured by Shin-Etsu Chemical Co. Ltd.), 10 weight parts of polyether-modified silicone oil (trade name "KF6015", manufactured by Shin-Etsu Chemical Co. Ltd.), and 5 weight parts of polyether-modified silicone oil (trade name "KF6016", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto the surface of an ionomer substrate (trade name "Himilan 1855", manufactured by Dupont-Mitsui Polychemicals Co., Ltd., thickness: 100 μm), using an applicator, and then cured at 140° C. for 2 minutes to obtain a 200 μm-thick, antifouling layer-attached substrate layer (antifouling layer (thickness: 100 μm)/substrate layer (thickness: 100 μm)).

<Production of Pressure-Sensitive Adhesive Layer)

80 weight parts of 2-ethylhexyl acrylate (manufactured by Toagosei Co., Ltd.), and 20 weight parts of N-vinyl-2-pyrrolidone (manufactured by Nippon Shokubai Co., Ltd.) were put into a reaction vessel equipped with a cooling tube, a nitrogen inlet tube, a thermometer and a stirring device. Then, 0.05 weight parts of 2,2-dimethoxy-1,2-diphenylethan-1-one (trade name "Irgacure 651", manufactured by BASF) as a photopolymerization initiator was put thereinto and dispersed therein, and, under a nitrogen stream, the resulting dispersion mixture was subjected to UV irradiation from thereabove, while being stirred, to convert a part of monomers into a polymer, thereby adjusting the viscosity thereof to a coatable level to obtain an acrylic monomer-polymer mixture. 10 weight parts of the acrylic polymer obtained in Production Example 1, and 0.32 weight parts of dipentaerythritol hexaacrylate (trade name "A-DPH", manufactured by Shin-Nakamura Chemical Co., Ltd.), were put into the obtained acrylic monomer-polymer mixture. The resulting resin composition was applied to the surface of a separator (trade name "MRF38", manufactured by Mitsubishi Plastics, Inc., thickness: 38 μm) using an applicator. Then, after bonding a cover separator (trade name "MRF38", manufactured by Mitsubishi Plastics, Inc., thickness: 38 μm) to the applied resin composition by a hand roller, the resin composition was irradiated with ultraviolet light from an ultraviolet lamp (ultraviolet illuminance: 3.4 mW/cm$^2$, cumulative dose: 2,000 mJ/cm$^2$) to obtain a 50 μm-thick pressure-sensitive adhesive composition.

<Production of Antifouling Layer-Including Pressure-Sensitive Adhesive Film>

The pressure-sensitive adhesive layer obtained in Inventive Example 1 was bonded to the substrate layer of the 200 μm-thick, antifouling layer-attached substrate layer (antifouling layer (thickness: 100 μm)/substrate layer (thickness: 100 μm)) obtained in Inventive Example 1, using a laminator to obtain an antifouling layer-including pressure-sensitive adhesive film consisting of "antifouling layer (thickness: 100 μm)/substrate layer (thickness: 100 μm)/pressure-sensitive adhesive layer (thickness: 50 μm)).

Inventive Example 2

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 45 weight parts of dimethyl silicone oil (trade name "KF96-100 cs", manufactured by Shin-Etsu Chemical Co. Ltd.), 20 weight parts of alkyl-modified silicone oil (trade name "KF415", manufactured by Shin-Etsu Chemical Co. Ltd.), and 10 weight parts of polyether-modified silicone oil (trade name "KF6015", manufactured by Shin-Etsu Chemical Co. Ltd.) were mixed together, and the resulting mixture was steered at room temperature (23° C.) for 5 minutes to obtain an antifouling layer-forming material liquid. The obtained antifouling layer-forming material liquid was applied onto the surface of an ionomer substrate (trade name "Himilan 1855", manufactured by Dupont-Mitsui Polychemicals Co., Ltd., thickness: 100 μm), using an applicator, and then cured at 140° C. for 2 minutes to obtain a 200 μm-thick, antifouling layer-attached substrate layer (antifouling layer (thickness: 100 μm)/substrate layer (thickness: 100 μm)).

<Production of Antifouling Layer-Including Pressure-Sensitive Adhesive Film>

The pressure-sensitive adhesive layer obtained in Inventive Example 1 was bonded to the substrate layer of the 200 μm-thick, antifouling layer-attached substrate layer (antifouling layer (thickness: 100 μm)/substrate layer (thickness: 100 μm)) obtained in Inventive Example 2, using a laminator to obtain an antifouling layer-including pressure-sensitive adhesive film consisting of "antifouling layer (thickness: 100 μm)/substrate layer (thickness: 100 μm)/pressure-sensitive adhesive layer (thickness: 50 μm)).

Inventive Example 3

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 40 weight parts of dimethyl silicone oil (trade name "KF96-100 cs", manufactured by Shin-Etsu Chemical Co. Ltd.), 20 weight parts of alkyl-modified silicone oil (trade name "KF415", manufactured by Shin-Etsu Chemical Co. Ltd.), and 10 weight parts of polyether-modified silicone oil (trade name "KF6013", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto the surface of an ionomer substrate (trade name "Himilan 1855", manufactured by Dupont-Mitsui Polychemicals Co., Ltd., thickness: 100 μm), using an applicator, and then cured at 140° C. for 2 minutes to obtain a 200 μm-thick, antifouling layer-attached substrate layer (antifouling layer (thickness: 100 μm)/substrate layer (thickness: 100 μm)).

<Production of Antifouling Layer-Including Pressure-Sensitive Adhesive Film>

The pressure-sensitive adhesive layer obtained in Inventive Example 1 was bonded to the substrate layer of the 200 μm-thick, antifouling layer-attached substrate layer (antifouling layer (thickness: 100 μm)/substrate layer (thickness: 100 μm)) obtained in Inventive Example 3, using a laminator to obtain an antifouling layer-including pressure-sensitive adhesive film consisting of "antifouling layer (thickness: 100 μm)/substrate layer (thickness: 100 μm)/pressure-sensitive adhesive layer (thickness: 50 μm)).

Inventive Example 4

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 40 weight parts of dimethyl silicone oil (trade name "KF96-100 cs", manufactured by Shin-Etsu Chemical Co. Ltd.), 20 weight parts of alkyl-modified silicone oil (trade name "KF415", manufactured by Shin-Etsu Chemical Co. Ltd.), and 10 weight parts of polyether-modified silicone oil (trade name "KF6017", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto the surface of an ionomer substrate (trade name "Himilan 1855", manufactured by Dupont-Mitsui Polychemicals Co., Ltd., thickness: 100 μm), using an applicator, and then cured at 140° C. for 2 minutes to obtain a 200 μm-thick, antifouling layer-attached substrate layer (antifouling layer (thickness: 100 μm)/substrate layer (thickness: 100 μm)).

<Production of Antifouling Layer-Including Pressure-Sensitive Adhesive Film>

The pressure-sensitive adhesive layer obtained in Inventive Example 1 was bonded to the substrate layer of the 200 μm-thick, antifouling layer-attached substrate layer (antifouling layer (thickness: 100 μm)/substrate layer (thickness: 100 μm)) obtained in Inventive Example 4, using a laminator to obtain an antifouling layer-including pressure-sensitive adhesive film consisting of "antifouling layer (thickness: 100 μm)/substrate layer (thickness: 100 μm)/pressure-sensitive adhesive layer (thickness: 50 μm)).

Inventive Example 5

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 65 weight parts of dimethyl silicone oil (trade name "KF96-100 cs", manufactured by Shin-Etsu Chemical Co. Ltd.), and 5 weight parts of polyether-modified silicone oil (trade name "KF6016", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto the surface of an ionomer substrate (trade name "Himilan 1855", manufactured by Dupont-Mitsui Polychemicals Co., Ltd., thickness: 100 μm), using an applicator, and then cured at 140° C. for 2 minutes to obtain a 200 μm-thick, antifouling layer-attached substrate layer (antifouling layer (thickness: 100 μm)/substrate layer (thickness: 100 μm)).

<Production of Antifouling Layer-Including Pressure-Sensitive Adhesive Film>

The pressure-sensitive adhesive layer obtained in Inventive Example 1 was bonded to the substrate layer of the 200

μm-thick, antifouling layer-attached substrate layer (antifouling layer (thickness: 100 μm)/substrate layer (thickness: 100 μm)) obtained in Inventive Example 5, using a laminator to obtain an antifouling layer-including pressure-sensitive adhesive film consisting of "antifouling layer (thickness: 100 μm)/substrate layer (thickness: 100 μm)/pressure-sensitive adhesive layer (thickness: 50 μm))".

Inventive Example 6

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 35 weight parts of dimethyl silicone oil (trade name "KF96-100 cs", manufactured by Shin-Etsu Chemical Co. Ltd.), 8 weight parts of alkyl-modified silicone oil (trade name "KF415", manufactured by Shin-Etsu Chemical Co. Ltd.), 4 weight parts of polyether-modified silicone oil (trade name "KF6015", manufactured by Shin-Etsu Chemical Co. Ltd.), and 2 weight parts of polyether-modified silicone oil (trade name "KF6016", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto the surface of an ionomer substrate (trade name "Himilan 1855", manufactured by Dupont-Mitsui Polychemicals Co., Ltd., thickness: 100 μm), using an applicator, and then cured at 140° C. for 2 minutes to obtain a 200 μm-thick, antifouling layer-attached substrate layer (antifouling layer (thickness: 100 μm)/substrate layer (thickness: 100 μm)).

<Production of Antifouling Layer-Including Pressure-Sensitive Adhesive Film>

The pressure-sensitive adhesive layer obtained in Inventive Example 1 was bonded to the substrate layer of the 200 μm-thick, antifouling layer-attached substrate layer (antifouling layer (thickness: 100 μm)/substrate layer (thickness: 100 μm)) obtained in Inventive Example 6, using a laminator to obtain an antifouling layer-including pressure-sensitive adhesive film consisting of "antifouling layer (thickness: 100 μm)/substrate layer (thickness: 100 μm)/pressure-sensitive adhesive layer (thickness: 50 μm))".

Inventive Example 7

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 35 weight parts of dimethyl silicone oil (trade name "KF96-100 cs", manufactured by Shin-Etsu Chemical Co. Ltd.), 20 weight parts of alkyl-modified silicone oil (trade name "KF415", manufactured by Shin-Etsu Chemical Co. Ltd.), 10 weight parts of polyether-modified silicone oil (trade name "KF6015", manufactured by Shin-Etsu Chemical Co. Ltd.), and 5 weight parts of polyether-modified silicone oil (trade name "KF6016", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto the surface of an ionomer substrate (trade name "Himilan 1855", manufactured by Dupont-Mitsui Polychemicals Co., Ltd., thickness: 100 μm), using an applicator, and then cured at 140° C. for 2 minutes to obtain a 150 μm-thick, antifouling layer-attached substrate layer (antifouling layer (thickness: 50 μm)/substrate layer (thickness: 100 μm)).

<Production of Antifouling Layer-Including Pressure-Sensitive Adhesive Film>

The pressure-sensitive adhesive layer obtained in Inventive Example 1 was bonded to the substrate layer of the 150 μm-thick, antifouling layer-attached substrate layer (antifouling layer (thickness: 50 μm)/substrate layer (thickness: 100 μm)) obtained in Inventive Example 7, using a laminator to obtain an antifouling layer-including pressure-sensitive adhesive film consisting of "antifouling layer (thickness: 50 μm)/substrate layer (thickness: 100 μm)/pressure-sensitive adhesive layer (thickness: 50 μm))".

Inventive Example 8

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 35 weight parts of dimethyl silicone oil (trade name "KF96-100 cs", manufactured by Shin-Etsu Chemical Co. Ltd.), 20 weight parts of alkyl-modified silicone oil (trade name "KF415", manufactured by Shin-Etsu Chemical Co. Ltd.), 10 weight parts of polyether-modified silicone oil (trade name "KF6015", manufactured by Shin-Etsu Chemical Co. Ltd.), and 5 weight parts of polyether-modified silicone oil (trade name "KF6016", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto the surface of an ionomer substrate (trade name "Himilan 1855", manufactured by Dupont-Mitsui Polychemicals Co., Ltd., thickness: 100 μm), using an applicator, and then cured at 140° C. for 2 minutes to obtain a 300 μm-thick, antifouling layer-attached substrate layer (antifouling layer (thickness: 200 μm)/substrate layer (thickness: 100 μm)).

<Production of Antifouling Layer-Including Pressure-Sensitive Adhesive Film>

The pressure-sensitive adhesive layer obtained in Inventive Example 1 was bonded to the substrate layer of the 300 μm-thick, antifouling layer-attached substrate layer (antifouling layer (thickness: 200 μm)/substrate layer (thickness: 100 μm)) obtained in Inventive Example 8, using a laminator to obtain an antifouling layer-including pressure-sensitive adhesive film consisting of "antifouling layer (thickness: 200 μm)/substrate layer (thickness: 100 μm)/pressure-sensitive adhesive layer (thickness: 50 μm))".

Inventive Example 9

<Production of Laminate of Antifouling Layer/Substrate Layer>

A 200 μm-thick, antifouling layer-attached substrate layer (antifouling layer (thickness: 100 μm)/substrate layer (thickness: 100 μm)) was obtained in the same manner as that in Inventive Example 1.

<Production of Pressure-Sensitive Adhesive Layer)

10 weight parts of the acrylic polymer obtained in Production Example 1, and 0.32 weight parts of dipentaerythritol hexaacrylate (trade name "A-DPH", manufactured by Shin-Nakamura Chemical Co., Ltd.), were put into the acrylic monomer-polymer mixture obtained in Inventive Example 1. The resulting resin composition was applied to the surface of a separator (trade name "MRF38", manufactured by Mitsubishi Plastics, Inc., thickness: 38 µm) using an applicator. Then, after bonding a cover separator (trade name "MRF38", manufactured by Mitsubishi Plastics, Inc., thickness: 38 µm) to the applied resin composition by a hand roller, the resin composition was irradiated with ultraviolet light from an ultraviolet lamp (ultraviolet illuminance: 3.4 mW/cm$^2$, cumulative dose: 2,000 mJ/cm$^2$) to obtain a 20 µm-thick pressure-sensitive adhesive composition.

<Production of Antifouling Layer-Including Pressure-Sensitive Adhesive Film>

The pressure-sensitive adhesive layer obtained in Inventive Example 9 was bonded to the substrate layer of the 200 µm-thick, antifouling layer-attached substrate layer (antifouling layer (thickness: 100 µm)/substrate layer (thickness: 100 µm)) obtained in Inventive Example 9, using a laminator to obtain an antifouling layer-including pressure-sensitive adhesive film consisting of "antifouling layer (thickness: 100 µm)/substrate layer (thickness: 100 µm)/pressure-sensitive adhesive layer (thickness: 20 µm)).

Inventive Example 10

<Production of Laminate of Antifouling Layer/Substrate Layer>

A 200 µm-thick, antifouling layer-attached substrate layer (antifouling layer (thickness: 100 µm)/substrate layer (thickness: 100 µm)) was obtained in the same manner as that in Inventive Example 1.

<Production of Pressure-Sensitive Adhesive Layer)

10 weight parts of the acrylic polymer obtained in Production Example 1, and 0.32 weight parts of dipentaerythritol hexaacrylate (trade name "A-DPH", manufactured by Shin-Nakamura Chemical Co., Ltd.), were put into the acrylic monomer-polymer mixture obtained in Inventive Example 1. The resulting resin composition was applied to the surface of a separator (trade name "MRF38", manufactured by Mitsubishi Plastics, Inc., thickness: 38 µm) using an applicator. Then, after bonding a cover separator (trade name "MRF38", manufactured by Mitsubishi Plastics, Inc., thickness: 38 µm) to the applied resin composition by a hand roller, the resin composition was irradiated with ultraviolet light from an ultraviolet lamp (ultraviolet illuminance: 3.4 mW/cm$^2$, cumulative dose: 2,000 mJ/cm$^2$) to obtain a 300 µm-thick pressure-sensitive adhesive composition.

<Production of Antifouling Layer-Including Pressure-Sensitive Adhesive Film>

The pressure-sensitive adhesive layer obtained in Inventive Example 10 was bonded to the substrate layer of the 200 µm-thick, antifouling layer-attached substrate layer (antifouling layer (thickness: 100 µm)/substrate layer (thickness: 100 µm)) obtained in Inventive Example 10, using a laminator to obtain an antifouling layer-including pressure-sensitive adhesive film consisting of "antifouling layer (thickness: 100 µm)/substrate layer (thickness: 100 µm)/pressure-sensitive adhesive layer (thickness: 300 µm)).

Inventive Example 11

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 35 weight parts of dimethyl silicone oil (trade name "KF96-100 cs", manufactured by Shin-Etsu Chemical Co. Ltd.), 20 weight parts of alkyl-modified silicone oil (trade name "KF415", manufactured by Shin-Etsu Chemical Co. Ltd.), 10 weight parts of polyether-modified silicone oil (trade name "KF6015", manufactured by Shin-Etsu Chemical Co. Ltd.), and 5 weight parts of polyether-modified silicone oil (trade name "KF6016", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto the surface of an ionomer substrate (trade name "Himilan 1855", manufactured by Dupont-Mitsui Polychemicals Co., Ltd., thickness: 50 µm), using an applicator, and then cured at 140° C. for 2 minutes to obtain a 150 µm-thick, antifouling layer-attached substrate layer (antifouling layer (thickness: 100 µm)/substrate layer (thickness: 50 µm)).

<Production of Antifouling Layer-Including Pressure-Sensitive Adhesive Film>

The pressure-sensitive adhesive layer obtained in Inventive Example 1 was bonded to the substrate layer of the 150 µm-thick, antifouling layer-attached substrate layer (antifouling layer (thickness: 100 µm)/substrate layer (thickness: 50 µm)) obtained in Inventive Example 11, using a laminator to obtain an antifouling layer-including pressure-sensitive adhesive film consisting of "antifouling layer (thickness: 100 µm)/substrate layer (thickness: 50 µm)/pressure-sensitive adhesive layer (thickness: 50 µm)).

Inventive Example 12

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 35 weight parts of dimethyl silicone oil (trade name "KF96-100 cs", manufactured by Shin-Etsu Chemical Co. Ltd.), 20 weight parts of alkyl-modified silicone oil (trade name "KF415", manufactured by Shin-Etsu Chemical Co. Ltd.), 10 weight parts of polyether-modified silicone oil (trade name "KF6015", manufactured by Shin-Etsu Chemical Co. Ltd.), and 5 weight parts of polyether-modified silicone oil (trade name "KF6016", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto the surface of an ionomer substrate (trade name "Himilan 1855", manufactured by Dupont-Mitsui Polychemicals Co., Ltd., thickness: 300 µm), using an applicator, and then cured at 140° C. for 2 minutes to obtain a 400 µm-thick, antifouling layer-attached substrate layer (antifouling layer (thickness: 100 µm)/substrate layer (thickness: 300 µm)).

<Production of Antifouling Layer-Including Pressure-Sensitive Adhesive Film>

The pressure-sensitive adhesive layer obtained in Inventive Example 1 was bonded to the substrate layer of the 400 µm-thick, antifouling layer-attached substrate layer (antifouling layer (thickness: 100 µm)/substrate layer (thickness: 300 µm)) obtained in Inventive Example 12, using a laminator to obtain an antifouling layer-including pressure-sensitive adhesive film consisting of "antifouling layer (thickness: 100 μm)/substrate layer (thickness: 300 μm)/pressure-sensitive adhesive layer (thickness: 50 μm)).

Inventive Example 13

<Production of Substrate Layer>

A solution obtained by dissolving 25 weight % of a copolymer of polyvinyl chloride and polyvinyl acetate (trade name "SOLBIN CH", manufactured by Shin-Etsu Chemical Co. Ltd.) in 75 weight parts of methyl ethyl ketone was applied to the surface of a separator (trade name "MRF38" manufactured by Mitsubishi Plastics, Inc., thickness: 38 μm) using an applicator, and then dried at 120° C. for 2 minutes to obtain a 30 μm-thick substrate layer. Subsequently, a mixed liquid obtained by mixing 100 weight parts of polyethylene-based ionomer resin emulsion (SA100, manufactured by Mitsui Chemicals, Inc.), 100 weight parts of colloidal silica (ADELITE AT-50, manufactured by ADEKA Corporation), and 0.5 weight parts of surfactant (Surfynol 420, manufactured by Nissin Chemical Co., Ltd.) was applied onto the substrate layer obtained in the above manner, using a wire bar #6, and then dried at 60° C. for 1 minute to obtain a primer-treated substrate layer.

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 35 weight parts of dimethyl silicone oil (trade name "KF96-100 cs", manufactured by Shin-Etsu Chemical Co. Ltd.), 20 weight parts of alkyl-modified silicone oil (trade name "KF415", manufactured by Shin-Etsu Chemical Co. Ltd.), 10 weight parts of polyether-modified silicone oil (trade name "KF6015", manufactured by Shin-Etsu Chemical Co. Ltd.), and 5 weight parts of polyether-modified silicone oil (trade name "KF6016", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto a primer-treated surface of the primer-treated substrate obtained in Inventive Example 13, using an applicator, and then cured at 140° C. for 2 minutes to obtain a 130 μm-thick, antifouling layer-attached substrate layer (antifouling layer (thickness: 100 μm)/substrate layer (thickness: 30 μm)).

<Production of Antifouling Layer-Including Pressure-Sensitive Adhesive Film>

The pressure-sensitive adhesive layer obtained in Inventive Example 1 was bonded to the substrate layer of the 130 μm-thick, antifouling layer-attached substrate layer (antifouling layer (thickness: 100 μm)/substrate layer (thickness: 30 μm)) obtained in Inventive Example 13, using a laminator to obtain an antifouling layer-including pressure-sensitive adhesive film consisting of "antifouling layer (thickness: 100 μm)/substrate layer (thickness: 30 μm)/pressure-sensitive adhesive layer (thickness: 50 μm)).

Inventive Example 14

<Production of Substrate Layer>

100 weight parts of vinyl chloride resin (trade name "TH-1000", manufactured by Taiyo Vinyl Corporation), and 40 weight parts of di-isononyl phthalate (J-PLUS Co., Ltd.) were kneaded by a Banbury mixer, and rolled by a calendar roll to obtain a 100 μm-thick polyvinyl chloride substrate. Subsequently, a mixed liquid obtained by mixing 100 weight parts of polyethylene-based ionomer resin emulsion (SA100, manufactured by Mitsui Chemicals, Inc.), 100 weight parts of colloidal silica (ADELITE AT-50, manufactured by ADEKA Corporation), and 0.5 weight parts of surfactant (Surfynol 420, manufactured by Nissin Chemical Co., Ltd.) was applied onto the polyvinyl chloride substrate obtained in the above manner, using a wire bar #6, and then dried at 60° C. for 1 minute to obtain a primer-treated substrate layer.

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 35 weight parts of dimethyl silicone oil (trade name "KF96-100 cs", manufactured by Shin-Etsu Chemical Co. Ltd.), 20 weight parts of alkyl-modified silicone oil (trade name "KF415", manufactured by Shin-Etsu Chemical Co. Ltd.), 10 weight parts of polyether-modified silicone oil (trade name "KF6015", manufactured by Shin-Etsu Chemical Co. Ltd.), and 5 weight parts of polyether-modified silicone oil (trade name "KF6016", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto a primer-treated surface of the primer-treated substrate obtained in Inventive Example 14, using an applicator, and then cured at 140° C. for 2 minutes to obtain a 200 μm-thick, antifouling layer-attached substrate layer (antifouling layer (thickness: 100 μm)/substrate layer (thickness: 100 μm)).

<Production of Antifouling Layer-Including Pressure-Sensitive Adhesive Film>

The pressure-sensitive adhesive layer obtained in Inventive Example 1 was bonded to the substrate layer of the 200 μm-thick, antifouling layer-attached substrate layer (antifouling layer (thickness: 100 μm)/substrate layer (thickness: 100 μm)) obtained in Inventive Example 14, using a laminator to obtain an antifouling layer-including pressure-sensitive adhesive film consisting of "antifouling layer (thickness: 100 μm)/substrate layer (thickness: 100 μm)/pressure-sensitive adhesive layer (thickness: 50 μm)).

Inventive Example 15

<Production of Substrate Layer>

A mixed liquid obtained by mixing 100 weight parts of polyethylene-based ionomer resin emulsion (SA100, manufactured by Mitsui Chemicals, Inc.), 100 weight parts of colloidal silica (ADELITE AT-50, manufactured by ADEKA Corporation), and 0.5 weight parts of surfactant (Surfynol 420, manufactured by Nissin Chemical Co., Ltd.) was applied onto a polyethylene terephthalate substrate (trade name "Lumirror 38 S10", manufactured by PANAC Corporation, thickness: 38 μm), using a wire bar #6, and then dried at 60° C. for 1 minute to obtain a primer-treated substrate layer.

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 35 weight parts of dimethyl silicone oil (trade name "KF96-100 cs", manufactured by Shin-Etsu Chemical Co. Ltd.), 20 weight parts of alkyl-modified silicone oil (trade name "KF415", manufactured by Shin- Etsu Chemical Co. Ltd.), 10 weight parts of polyether-modified silicone oil (trade name "KF6015", manufactured by Shin-Etsu Chemical Co. Ltd.), and 5 weight parts of polyether-modified silicone oil (trade name "KF6016", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto a primer-treated surface of the primer-treated substrate obtained in Inventive Example 15, using an applicator, and then cured at 140° C. for 2 minutes to obtain a 138 μm-thick, antifouling layer-attached substrate layer (antifouling layer (thickness: 100 μm)/substrate layer (thickness: 38 μm)).
<Production of Antifouling Layer-Including Pressure-Sensitive Adhesive Film>

The pressure-sensitive adhesive layer obtained in Inventive Example 1 was bonded to the substrate layer of the 138 μm-thick, antifouling layer-attached substrate layer (antifouling layer (thickness: 100 μm)/substrate layer (thickness: 38 μm)) obtained in Inventive Example 15, using a laminator to obtain an antifouling layer-including pressure-sensitive adhesive film consisting of "antifouling layer (thickness: 100 μm)/substrate layer (thickness: 38 μm)/pressure-sensitive adhesive layer (thickness: 50 μm)).

Inventive Example 16

<Production of Substrate Layer>

A mixed liquid obtained by mixing 100 weight parts of polyethylene-based ionomer resin emulsion (SA100, manufactured by Mitsui Chemicals, Inc.), 100 weight parts of colloidal silica (ADELITE AT-50, manufactured by ADEKA Corporation), and 0.5 weight parts of surfactant (Surfynol 420, manufactured by Nissin Chemical Co., Ltd.) was applied onto a polycarbonate-based polyurethane resin substrate (trade name "Esuma URS PXII", manufactured by Nihon Matai Co., Ltd., thickness of 100 μm), using a wire bar #6, and then dried at 60° C. for 1 minute to obtain a primer-treated substrate layer.
<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 35 weight parts of dimethyl silicone oil (trade name "KF96-100 cs", manufactured by Shin-Etsu Chemical Co. Ltd.), 20 weight parts of alkyl-modified silicone oil (trade name "KF415", manufactured by Shin-Etsu Chemical Co. Ltd.), 10 weight parts of polyether-modified silicone oil (trade name "KF6015", manufactured by Shin-Etsu Chemical Co. Ltd.), and 5 weight parts of polyether-modified silicone oil (trade name "KF6016", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto a primer-treated surface of the primer-treated substrate obtained in Inventive Example 16, using an applicator, and then cured at 140° C. for 2 minutes to obtain a 200 μm-thick, antifouling layer-attached substrate layer (antifouling layer (thickness: 100 μm)/substrate layer (thickness: 100 μm)).
<Production of Antifouling Layer-Including Pressure-Sensitive Adhesive Film>

The pressure-sensitive adhesive layer obtained in Inventive Example 1 was bonded to the substrate layer of the 300 μm-thick, antifouling layer-attached substrate layer (antifouling layer (thickness: 100 μm)/substrate layer (thickness: 100 μm)) obtained in Inventive Example 16, using a laminator to obtain an antifouling layer-including pressure-sensitive adhesive film consisting of "antifouling layer (thickness: 100 μm)/substrate layer (thickness: 100 μm)/pressure-sensitive adhesive layer (thickness: 50 μm)).

Inventive Example 17

<Production of Laminate of Antifouling Layer/Substrate Layer>

A 200 μm-thick, antifouling layer-attached substrate layer (antifouling layer (thickness: 100 μm)/substrate layer (thickness: 100 μm)) was obtained in the same manner as that in Inventive Example 16.
<Production of Pressure-Sensitive Adhesive Layer)

94 weight parts of 2-ethylhexyl acrylate (manufactured by Toagosei Co., Ltd.), and 6 weight parts of acrylic acid (manufactured by Toagosei Co., Ltd.) were put into a reaction vessel equipped with a cooling tube, a nitrogen inlet tube, a thermometer and a stirring device. Then, 0.05 weight parts of 2,2-dimethoxy-1,2-diphenylethan-1-one (trade name "Irgacure 651", manufactured by BASF) as a photo-polymerization initiator was put thereinto and dispersed therein, and, under a nitrogen stream, the resulting dispersion mixture was subjected to UV irradiation from there-above, while being stirred, to convert a part of monomers into a polymer, thereby adjusting the viscosity thereof to a coatable level to obtain an acrylic monomer-polymer mixture. 5 weight parts of the acrylic polymer obtained in Production Example 1, and 0.16 weight parts of 1,6-hexanediol diacrylate (trade name "A-HD-N", manufactured by Shin-Nakamura Chemical Co., Ltd.), were put into the obtained acrylic monomer-polymer mixture. The resulting resin composition was applied to the surface of a separator (trade name "MRF38" manufactured by Mitsubishi Plastics, Inc., thickness: 38 μm) using an applicator. Then, after bonding a cover separator (trade name "MRF38" manufactured by Mitsubishi Plastics, Inc., thickness: 38 μm) to the applied resin composition by a hand roller, the resin composition was irradiated with ultraviolet light from an ultraviolet lamp (ultraviolet illuminance: 3.4 mW/cm$^2$, cumulative dose: 2,000 mJ/cm$^2$) to obtain a 50 μm-thick pressure-sensitive adhesive composition.
<Production of Antifouling Layer-Including Pressure-Sensitive Adhesive Film>

The pressure-sensitive adhesive layer obtained in Inventive Example 17 was bonded to the substrate layer of the 200 μm-thick, antifouling layer-attached substrate layer (antifouling layer (thickness: 100 μm)/substrate layer (thickness: 100 μm)) obtained in Inventive Example 17, using a laminator to obtain an antifouling layer-including pressure-sensitive adhesive film consisting of "antifouling layer (thickness: 100 μm)/substrate layer (thickness: 100 μm)/pressure-sensitive adhesive layer (thickness: 50 μm)).

Inventive Example 18

<Production of Laminate of Antifouling Layer/Substrate Layer>

100 weight parts of silicone resin (condensed-type liquid silicone resin, trade name "KE-445", manufactured by Shin-Etsu Chemical Co. Ltd.), 65 weight parts of dimethyl silicone oil (trade name "KF96-100 cs", manufactured by Shin-Etsu Chemical Co. Ltd.), and 5 weight parts of polyether-modified silicone oil (trade name "KF6016", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto the surface of an ionomer substrate (trade name "Himilan 1855", manufactured by Dupont-Mitsui Polychemicals Co., Ltd., thickness: 100 μm), using an applicator, and then cured at room temperature (23° C.) for 24 hours to obtain a 200 μm-thick, antifouling layer-attached substrate layer (antifouling layer (thickness: 100 μm)/substrate layer (thickness: 100 μm)).

<Production of Antifouling Layer-Including Pressure-Sensitive Adhesive Film>

The pressure-sensitive adhesive layer obtained in Inventive Example 1 was bonded to the substrate layer of the 200 μm-thick, antifouling layer-attached substrate layer (antifouling layer (thickness: 100 μm)/substrate layer (thickness: 100 μm)) obtained in Inventive Example 18, using a laminator to obtain an antifouling layer-including pressure-sensitive adhesive film consisting of "antifouling layer (thickness: 100 μm)/substrate layer (thickness: 100 μm)/pressure-sensitive adhesive layer (thickness: 50 μm)).

Reference Example 1

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), and 70 weight parts of dimethyl silicone oil (trade name "KF96-100 cs", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto the surface of an ionomer substrate (trade name "Himilan 1855", manufactured by Dupont-Mitsui Polychemicals Co., Ltd., thickness: 100 μm), using an applicator, and then cured at 140° C. for 2 minutes to obtain a 200 μm-thick, antifouling layer-attached substrate layer (antifouling layer (thickness: 100 μm)/substrate layer (thickness: 100 μm)).

<Production of Antifouling Layer-Including Pressure-Sensitive Adhesive Film>

The pressure-sensitive adhesive layer obtained in Inventive Example 1 was bonded to the substrate layer of the 200 μm-thick, antifouling layer-attached substrate layer (antifouling layer (thickness: 100 μm)/substrate layer (thickness: 100 μm)) obtained in Reference Example 1, using a laminator to obtain an antifouling layer-including pressure-sensitive adhesive film consisting of "antifouling layer (thickness: 100 μm)/substrate layer (thickness: 100 μm)/pressure-sensitive adhesive layer (thickness: 50 μm)).

Reference Example 2

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 26 weight parts of dimethyl silicone oil (trade name "KF96-100 cs", manufactured by Shin-Etsu Chemical Co. Ltd.), 20 weight parts of alkyl-modified silicone oil (trade name "KF415", manufactured by Shin-Etsu Chemical Co. Ltd.), and 1 weight part of polyether-modified silicone oil (trade name "KF6016", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto the surface of an ionomer substrate (trade name "Himilan 1855", manufactured by Dupont-Mitsui Polychemicals Co., Ltd., thickness: 100 μm), using an applicator, and then cured at 140° C. for 2 minutes to obtain a 200 μm-thick, antifouling layer-attached substrate layer (antifouling layer (thickness: 100 μm)/substrate layer (thickness: 100 μm)).

<Production of Antifouling Layer-Including Pressure-Sensitive Adhesive Film>

The pressure-sensitive adhesive layer obtained in Inventive Example 1 was bonded to the substrate layer of the 200 μm-thick, antifouling layer-attached substrate layer (antifouling layer (thickness: 100 μm)/substrate layer (thickness: 100 μm)) obtained in Reference Example 2, using a laminator to obtain an antifouling layer-including pressure-sensitive adhesive film consisting of "antifouling layer (thickness: 100 μm)/substrate layer (thickness: 100 μm)/pressure-sensitive adhesive layer (thickness: 50 μm)).

Reference Example 3

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 35 weight parts of dimethyl silicone oil (trade name "KF96-100 cs", manufactured by Shin-Etsu Chemical Co. Ltd.), 20 weight parts of alkyl-modified silicone oil (trade name "KF415", manufactured by Shin-Etsu Chemical Co. Ltd.), 10 weight parts of polyether-modified silicone oil (trade name "KF6015", manufactured by Shin-Etsu Chemical Co. Ltd.), and 5 weight parts of polyether-modified silicone oil (trade name "KF6016", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto the surface of a polycarbonate-based polyurethane resin substrate (trade name "Esuma URS PXII", manufactured by Nihon Matai Co., Ltd., thickness of 100 μm), using an applicator, and then cured at 140° C. for 2 minutes to obtain a 200 μm-thick, antifouling layer-attached substrate layer (antifouling layer (thickness: 100 μm)/substrate layer (thickness: 100 μm)).

<Production of Antifouling Layer-Including Pressure-Sensitive Adhesive Film>

The pressure-sensitive adhesive layer obtained in Inventive Example 1 was bonded to the substrate layer of the 200 μm-thick, antifouling layer-attached substrate layer (antifouling layer (thickness: 100 μm)/substrate layer (thickness: 100 μm)) obtained in Reference Example 3, using a laminator to obtain an antifouling layer-including pressure-sensitive adhesive film consisting of "antifouling layer (thickness: 100 μm)/substrate layer (thickness: 100 μm)/pressure-sensitive adhesive layer (thickness: 50 μm)).

Reference Example 4

<Production of Substrate Layer>

A solution obtained by dissolving 25 weight % of a copolymer of polyvinyl chloride and polyvinyl acetate (trade name "SOLBIN CH", manufactured by Shin-Etsu Chemical Co. Ltd.) in 75 weight parts of methyl ethyl ketone was applied to the surface of a separator (trade name "MRF38" manufactured by Mitsubishi Plastics, Inc., thickness: 38 μm) using an applicator, and then dried at 120° C. for 2 minutes to obtain a 18 μm-thick substrate layer. Subsequently, a mixed liquid obtained by mixing 100 weight parts of polyethylene-based ionomer resin emulsion (SA100, manufactured by Mitsui Chemicals, Inc.), 100 weight parts of colloidal silica (ADELITE AT-50, manufactured by ADEKA Corporation), and 0.5 weight parts of surfactant (Surfynol 420, manufactured by Nissin Chemical Co., Ltd.) was applied onto the substrate layer obtained in the above manner, using a wire bar #6, and then dried at 60° C. for 1 minute to obtain a primer-treated substrate layer.

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 35 weight parts of dimethyl silicone oil (trade name "KF96-100 cs", manufactured by Shin-Etsu Chemical Co. Ltd.), 20 weight parts of alkyl-modified silicone oil (trade name "KF415", manufactured by Shin-Etsu Chemical Co. Ltd.), 10 weight parts of polyether-modified silicone oil (trade name "KF6015", manufactured by Shin-Etsu Chemical Co. Ltd.), and 5 weight parts of polyether-modified silicone oil (trade name "KF6016", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto a primer-treated surface of the primer-treated substrate obtained in Reference Example 4, using an applicator, and then cured at 140° C. for 2 minutes to obtain a 118 μm-thick, antifouling layer-attached substrate layer (antifouling layer (thickness: 100 μm)/substrate layer (thickness: 18 μm)).

<Production of Antifouling Layer-Including Pressure-Sensitive Adhesive Film>

The pressure-sensitive adhesive layer obtained in Inventive Example 1 was bonded to the substrate layer of the 118 μm-thick, antifouling layer-attached substrate layer (antifouling layer (thickness: 100 μm)/substrate layer (thickness: 18 μm)) obtained in Reference Example 4, using a laminator to obtain an antifouling layer-including pressure-sensitive adhesive film consisting of "antifouling layer (thickness: 100 μm)/substrate layer (thickness: 18 μm)/pressure-sensitive adhesive layer (thickness: 50 μm)).

Reference Example 5

<Production of Substrate Layer>

71 weight parts of isobornyl acrylate (trade name "IBXA", manufactured by Osaka Organic Chemical Industry Ltd.), 19 weight parts of n-butyl acrylate (manufactured by Toagosei Co., Ltd.), 10 weight parts of acrylic acid (manufactured by Toagosei Co., Ltd.), 68.4 weight parts of poly (oxy-tetramethylene) glycol) (trade name "PTMG 650", manufactured by Mitsubishi Chemical Corporation), and 0.01 weight parts of dibutyltin dilaurate as catalyst, were put into a reaction vessel equipped with a cooling tube, a nitrogen inlet tube, a thermometer and a stirring device. Then, 25.5 weight parts of hydrogenated xylylene diisocyanate (trade name "TAKENATE 600", manufactured by Mitsui Chemicals, Inc.) was dripped in the mixture under stirring to induce a reaction therein at 65° C. for 5 hours, thereby obtaining a polyurethane polymer-acrylic monomer mixture. Subsequently, 6.1 weight parts of hydroxyethyl acrylate (trade name "ACRYCS HEA", manufactured by Toagosei Co., Ltd.) was further put in the resulting mixture to induce a reaction therein at 65° C. for 1 hours, thereby obtaining an acryloyl group-terminated polyurethane polymer-acrylic monomer mixture. Subsequently, 1 weight part of 3-acryloyloxypropyl trimethoxysilane (trade name "KBM-5103", manufactured by Shin-Etsu Chemical Co., Ltd.), 0.25 weight part of diphenyl(2,4,6-trimethoxybenzoyl)phosphine oxide (trade name "Lucirin TPO", manufactured by BASF) as a photopolymerization initiator, 1.25 weight parts of a UV absorbing agent (trade name "TINUVIN 123", manufactured by BASF), and 0.6 weight part of an anti-oxidizing agent (trade name "TINUVIN 400", manufactured by BASF) were added to the acryloyl group-terminated polyurethane polymer-acrylic monomer mixture to obtain a syrup. Subsequently, the syrup was applied onto the surface of a separator (trade name "MRF38," manufactured by Mitsubishi Plastics, Inc., thickness: 38 μm), using an applicator, to form a 150 μm-thick base material syrup layer. After bonding a cover separator (trade name "MRF38", manufactured by Mitsubishi Plastics, Inc., thickness: 38 μm) to the base material syrup layer by a laminator, the base material syrup layer was irradiated with UV light from a UV lamp (UV irradiance: 3.4 mW/cm$^2$, cumulative dose: 2,000 mJ/cm$^2$ to obtain a 150 μm-thick substrate layer.

<Production of Laminate of Antifouling Layer/Substrate Layer>

100 weight parts of silicone resin (condensed-type liquid silicone resin, trade name "KE-445", manufactured by Shin-Etsu Chemical Co. Ltd.), and 10 weight parts of phenyl-modified silicone oil (trade name "KF50-100 cs", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto the surface of the substrate obtained in Reference Example 5, using an applicator, and then cured at 150° C. for 10 minutes to obtain a 300 μm-thick, antifouling layer-attached substrate layer (antifouling layer (thickness: 150 μm)/substrate layer (thickness: 150 μm)).

<Production of Pressure-Sensitive Adhesive Layer)

80 weight parts of 2-ethylhexyl acrylate (manufactured by Toagosei Co., Ltd.), and 20 weight parts of N-vinyl-2-pyrrolidone (manufactured by Nippon Shokubai Co., Ltd.) were put into a reaction vessel equipped with a cooling tube, a nitrogen inlet tube, a thermometer and a stirring device. Then, 0.05 weight parts of 2,2-dimethoxy-1,2-diphenylethan-1-one (trade name "Irgacure 651", manufactured by BASF) as a photopolymerization initiator was put thereinto and dispersed therein, and, under a nitrogen stream, the resulting dispersion mixture was subjected to UV irradiation from thereabove, while being stirred, to convert a part of monomers into a polymer, thereby adjusting the viscosity thereof to a coatable level to obtain an acrylic monomer-polymer mixture. 10 weight parts of the acrylic polymer obtained in Production Example 1, and 0.08 weight parts of 1,6-hexanediol diacrylate (trade name "A-HD-N", manufactured by Shin-Nakamura Chemical Co., Ltd.), were put into the obtained acrylic monomer-polymer mixture. The resulting resin composition was applied to the surface of a separator (trade name "MRF38", manufactured by Mitsubishi Plastics, Inc., thickness: 38 μm) using an applicator. Then, after bonding a cover separator (trade name "MRF38", manufactured by Mitsubishi Plastics, Inc., thickness: 38 μm) to the applied resin composition by a hand roller, the resin composition was irradiated with ultraviolet light from an ultraviolet lamp (ultraviolet illuminance: 3.4 mW/cm$^2$, cumulative dose: 2,000 mJ/cm$^2$) to obtain a 50 μm-thick pressure-sensitive adhesive composition.

<Production of Antifouling Layer-Including Pressure-Sensitive Adhesive Film>

The pressure-sensitive adhesive layer obtained in Reference Example 5 was bonded to the substrate layer of the 300 μm-thick, antifouling layer-attached substrate layer (antifouling layer (thickness: 150 μm)/substrate layer (thickness: 150 μm)) obtained in Reference Example 5, using a laminator to obtain an antifouling layer-including pressure-sensitive adhesive film consisting of "antifouling layer (thickness: 150 μm)/substrate layer (thickness: 150 μm)/pressure-sensitive adhesive layer (thickness: 50 μm)).

Reference Example 6

<Production of Laminate of Antifouling Layer/Substrate Layer>

100 weight parts (agent A: 50 weight parts, agent B: 50 weight parts) of silicone resin (addition-type liquid silicone resin, trade name "KE-1950", manufactured by Shin-Etsu Chemical Co. Ltd.), 60 weight parts of dimethyl silicone oil (trade name "KF96-100 cs", manufactured by Shin-Etsu Chemical Co. Ltd.), 30 weight parts of polyether-modified silicone oil (trade name "KF6017", manufactured by Shin-Etsu Chemical Co. Ltd.), 2 weight parts of a UV absorbing agent (trade name "TINUVIN 571", manufactured by BASF), 1 weight part of nano-silica (trade name "AEROSIL RX-300", manufactured by Nippon Aerosil Co., Ltd.), and 5 weight parts of liquid paraffin (manufactured by KISHIDA CHEMICAL Co., Ltd.), were mixed together, and the resulting mixture was steered at room temperature (23° C.) for 5 minutes to obtain an antifouling layer-forming material liquid. The obtained antifouling layer-forming material liquid was applied onto the surface of a polycarbonate-based polyurethane resin substrate (trade name "Higress DUS451", manufactured by Sheedom Co., Ltd., thickness: 100 μm), using an applicator, and then cured at 140° C. for 2 minutes to obtain a 200 μm-thick, antifouling layer-attached substrate layer (antifouling layer (thickness: 100 μm)/substrate layer (thickness: 100 μm)).

<Production of Antifouling Layer-Including Pressure-Sensitive Adhesive Film>

The pressure-sensitive adhesive layer obtained in Inventive Example 17 was bonded to the substrate layer of the 200 μm-thick, antifouling layer-attached substrate layer (antifouling layer (thickness: 100 μm)/substrate layer (thickness: 100 μm)) obtained in Reference Example 6, using a laminator to obtain an antifouling layer-including pressure-sensitive adhesive film consisting of "antifouling layer (thickness: 100 μm)/substrate layer (thickness: 100 μm)/pressure-sensitive adhesive layer (thickness: 50 μm))".

Reference Example 7

<Production of Laminate of Antifouling Layer/Substrate Layer>

100 weight parts (agent A: 50 weight parts, agent B: 50 weight parts) of silicone resin (addition-type liquid silicone resin, trade name "KE-1950", manufactured by Shin-Etsu Chemical Co. Ltd.), 75 weight parts of dimethyl silicone oil (trade name "KF96-100 cs", manufactured by Shin-Etsu Chemical Co. Ltd.), 5 weight parts of polyether-modified silicone oil (trade name "KF6017", manufactured by Shin-Etsu Chemical Co. Ltd.), 2 weight parts of a UV absorbing agent (trade name "TINUVIN 571", manufactured by BASF), 0.25 weight part of a curing catalyst (trade name "CATPL-50T", manufactured by Shin-Etsu Chemical Co. Ltd.), and 5 weight parts of liquid paraffin (manufactured by KISHIDA CHEMICAL Co., Ltd.), were mixed together, and the resulting mixture was steered at room temperature (23° C.) for 5 minutes to obtain an antifouling layer-forming material liquid. The obtained antifouling layer-forming material liquid was applied onto the surface of a polycarbonate-based polyurethane resin substrate (trade name "Higress DUS451", manufactured by Sheedom Co., Ltd., thickness: 100 μm), using an applicator, and then cured at 140° C. for 2 minutes to obtain a 200 μm-thick, antifouling layer-attached substrate layer (antifouling layer (thickness: 100 μm)/substrate layer (thickness: 100 μm)).

<Production of Pressure-Sensitive Adhesive Layer>

90 weight parts of 2-ethylhexyl acrylate (manufactured by Toagosei Co., Ltd.), and 10 weight parts of acrylic acid (manufactured by Toagosei Co., Ltd.) were put into a reaction vessel equipped with a cooling tube, a nitrogen inlet tube, a thermometer and a stirring device. Then, 0.05 weight parts of 2,2-dimethoxy-1,2-diphenylethan-1-one (trade name "Irgacure 651", manufactured by BASF) as a photopolymerization initiator was put thereinto and dispersed therein, and, under a nitrogen stream, the resulting dispersion mixture was subjected to UV irradiation from there-above, while being stirred, to convert a part of monomers into a polymer, thereby adjusting the viscosity thereof to a coatable level to obtain an acrylic monomer-polymer mixture. 0.08 weight parts of 1,6-hexanediol diacrylate (trade name "A-HD-N", manufactured by Shin-Nakamura Chemical Co., Ltd.), was put into the obtained acrylic monomer-polymer mixture. The resulting resin composition was applied to the surface of a separator (trade name "MRF38" manufactured by Mitsubishi Plastics, Inc., thickness: 38 μm) using an applicator. Then, after bonding a cover separator (trade name "MRF38" manufactured by Mitsubishi Plastics, Inc., thickness: 38 μm) to the applied resin composition by a hand roller, the resin composition was irradiated with ultraviolet light from an ultraviolet lamp (ultraviolet illuminance: 3.4 mW/cm$^2$, cumulative dose: 2,000 mJ/cm$^2$) to obtain a 50 μm-thick pressure-sensitive adhesive composition.

<Production of Antifouling Layer-Including Pressure-Sensitive Adhesive Film>

The pressure-sensitive adhesive layer obtained in Reference Example 7 was bonded to the substrate layer of the 200 μm-thick, antifouling layer-attached substrate layer (antifouling layer (thickness: 100 μm)/substrate layer (thickness: 100 μm)) obtained in Reference Example 7, using a laminator to obtain an antifouling layer-including pressure-sensitive adhesive film consisting of "antifouling layer (thickness: 100 μm)/substrate layer (thickness: 100 μm)/pressure-sensitive adhesive layer (thickness: 50 μm))".

Reference Example 8

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 70 weight parts of dimethyl silicone oil (trade name "KF96-100 cs", manufactured by Shin-Etsu Chemical Co. Ltd.), and 20 weight parts of polyether-modified silicone oil (trade name "KF6017", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto the surface of an ionomer substrate (trade name "Himilan 1855", manufactured by Dupont-Mitsui Polychemicals Co., Ltd., thickness: 100 μm), using an applicator, and then cured at 140° C. for 2 minutes to obtain a 200 μm-thick, antifouling layer-attached substrate layer (antifouling layer (thickness: 100 μm)/substrate layer (thickness: 100 μm)).

90 weight parts of 2-ethylhexyl acrylate (manufactured by Toagosei Co., Ltd.), and 10 weight parts of acrylic acid (manufactured by Toagosei Co., Ltd.) were put into a reaction vessel equipped with a cooling tube, a nitrogen inlet tube, a thermometer and a stirring device. Then, 0.05 weight parts of 2,2-dimethoxy-1,2-diphenylethan-1-one (trade name "Irgacure 651", manufactured by BASF) as a photo-polymerization initiator was put thereinto and dispersed therein, and, under a nitrogen stream, the resulting dispersion mixture was subjected to UV irradiation from thereabove, while being stirred, to convert a part of monomers into a polymer, thereby adjusting the viscosity thereof to a coatable level to obtain an acrylic monomer-polymer mixture. 5 weight parts of the acrylic polymer obtained in Production Example 1, and 0.08 weight parts of 1,6-hexanediol diacrylate (trade name "A-HD-N", manufactured by Shin-Nakamura Chemical Co., Ltd.), were put into the obtained acrylic monomer-polymer mixture. The resulting resin composition was applied to the surface of a separator (trade name "MRF38" manufactured by Mitsubishi Plastics, Inc., thickness: 38 μm) using an applicator. Then, after bonding a cover separator (trade name "MRF38" manufactured by Mitsubishi Plastics, Inc., thickness: 38 μm) to the applied resin composition by a hand roller, the resin composition was irradiated with ultraviolet light from an ultraviolet lamp (ultraviolet illuminance: 3.4 mW/cm$^2$, cumulative dose: 2,000 mJ/cm$^2$) to obtain a 50 μm-thick pressure-sensitive adhesive composition.

<Production of Antifouling Layer-Including Pressure-Sensitive Adhesive Film>

The pressure-sensitive adhesive layer obtained in Reference Example 8 was bonded to the substrate layer of the 200 μm-thick, antifouling layer-attached substrate layer (antifouling layer (thickness: 100 μm)/substrate layer (thickness: 100 μm)) obtained in Reference Example 8, using a laminator to obtain an antifouling layer-including pressure-sensitive adhesive film consisting of "antifouling layer (thickness: 100 μm)/substrate layer (thickness: 100 μm)/pressure-sensitive adhesive layer (thickness: 50 μm))".

Properties of the antifouling layer-including pressure-sensitive adhesive film (aquatic organism adherence preventive film) required when used in the submersible sensor unit such as the acoustic Doppler current profiler (ADCP) or the like include; (1) a property of keeping aquatic organisms from adhering thereto even at a low flow velocity; (2) a property of being peelable off from an adherend, for the purpose of film replacement; and (3) a property of being free from peel-off of the antifouling layer of the film even after long-term use (assumed period: about 6 months).

With regard to the property of keeping aquatic organisms from adhering thereto even at a low flow velocity, the antifouling layer-including pressure-sensitive adhesive film was subjected to measurement of a water contact angle. With regard to the property of being peelable off from an adherend, the antifouling layer-including pressure-sensitive adhesive film was subjected to measurement of the ratio of a breaking strength to an adhesive force thereof. With regard to the property of being free from peel-off of the antifouling layer from the substrate layer of the film, the antifouling layer-including pressure-sensitive adhesive film was subjected to a cross-cut test. An evaluation method for each of the properties is as follows.

Each of the antifouling layer-including pressure-sensitive adhesive films obtained in the above Inventive and Reference Examples was subjected to the following evaluations. The result is shown in Table 2.

TABLE 2

| | Water Contact Angle (°) | | Cross-Cut | Tensile Breaking Strength after | Adhesive Force | Ratio of Tensile | |
|---|---|---|---|---|---|---|---|
| | Initial | After immersion in methanol for 20 min | (Number of peeled cells) | 60° C. × 4 days (N/20 mm) | after 60° C. × 4 days (N/20 mm) | Breaking Strength to Adhesive Force | Peelability |
| Inventive Example 1 | 25.0 | 50.1 | 0/100 | 64.7 | 7.5 | 8.6 | Peeled off without breaking |
| Inventive Example 2 | 43.1 | 56.0 | 0/100 | 63.7 | 7.3 | 8.7 | Peeled off without breaking |
| Inventive Example 3 | 42.2 | 57.0 | 0/100 | 66.1 | 7.7 | 8.6 | Peeled off without breaking |
| Inventive Example 4 | 46.5 | 67.5 | 0/100 | 65.5 | 8.4 | 7.8 | Peeled off without breaking |
| Inventive Example 5 | 43.3 | 58.2 | 0/100 | 63.0 | 7.8 | 8.1 | Peeled off without breaking |
| Inventive Example 6 | 56.7 | 69.5 | 0/100 | 62.1 | 7.3 | 8.5 | Peeled off without breaking |
| Inventive Example 7 | 24.5 | 48.2 | 0/100 | 63.0 | 7.8 | 8.1 | Peeled off without breaking |
| Inventive Example 8 | 23.8 | 47.8 | 0/100 | 66.3 | 8.1 | 8.2 | Peeled off without breaking |
| Inventive Example 9 | 23.7 | 48.4 | 0/100 | 66.4 | 6.2 | 10.7 | Peeled off without breaking |
| Inventive Example 10 | 24.5 | 49.7 | 0/100 | 63.5 | 22.0 | 2.9 | Peeled off without breaking |
| Inventive Example 11 | 24.2 | 48.5 | 0/100 | 39.9 | 13.5 | 3.0 | Peeled off without breaking |
| Inventive Example 12 | 24.8 | 49.6 | 0/100 | 198.0 | 11.6 | 17.1 | Peeled off without breaking |

TABLE 2-continued

| | Water Contact Angle (°) | | Cross-Cut | Tensile Breaking Strength after | Adhesive Force | Ratio of Tensile | |
|---|---|---|---|---|---|---|---|
| | Initial | After immersion in methanol for 20 min | (Number of peeled cells) | 60° C. × 4 days (N/20 mm) | after 60° C. × 4 days (N/20 mm) | Breaking Strength to Adhesive Force | Peelability |
| Inventive Example 13 | 23.7 | 49.0 | 0/100 | 27.2 | 18.0 | 1.5 | Peeled off without breaking |
| Inventive Example 14 | 25.3 | 51.2 | 0/100 | 53.7 | 8.5 | 6.3 | Peeled off without breaking |
| Inventive Example 15 | 25.5 | 52.8 | 0/100 | 142.4 | 17.5 | 8.1 | Peeled off without breaking |
| Inventive Example 16 | 24.8 | 49.3 | 0/100 | 101.1 | 12.0 | 8.4 | Peeled off without breaking |
| Inventive Example 17 | 25.1 | 50.6 | 0/100 | 98.2 | 11.8 | 8.3 | Peeled off without breaking |
| Inventive Example 18 | 40.2 | 55.2 | 0/100 | 63.5 | 7.4 | 8.6 | Peeled off without breaking |
| Reference Example 1 | 103.0 | 103.2 | 0/100 | 62.4 | 8.2 | 7.6 | Peeled off without breaking |
| Reference Example 2 | 74.0 | 91.3 | 0/100 | 65.6 | 8.4 | 7.8 | Peeled off without breaking |
| Reference Example 3 | 24.8 | 49.4 | 100/100 | 110.3 | 9.0 | 12.3 | Peeled off without breaking |
| Reference Example 4 | 24.5 | 49.7 | 0/100 | 14.5 | 12.5 | 1.2 | Broke during peeling |
| Reference Example 5 | 98.7 | 96.6 | 0/100 | 89.7 | 10.5 | 8.5 | Peeled off without breaking |
| Reference Example 6 | 49.5 | 56.7 | 100/100 | 107.1 | 11.3 | 9.5 | Peeled off without breaking |
| Reference Example 7 | 65.4 | 82.7 | 0/100 | 109.3 | 14.6 | 7.5 | Peeled off without breaking |
| Reference Example 8 | 52.3 | 62.7 | 0/100 | 67.8 | Non-measureable | — | Pressure-sensitive adhesive remained on adherend |

(Water Contact Angle in Initial State)

Each evaluation sample cut into a size of 10 mm×30 mm was fixed onto a glass plate by a double-faced adhesive tape, and set in a contact angle meter (Model: DROPMASTER-701, manufactured by Kyowa interface Science Co., Ltd.). A 2.0 μL droplet of distilled water was attached to the surface of the sample, and, after the elapse of 300 seconds since the start of the attachment, a contact angle (room temperature (23° C.) was measured by a measurement mode of a θ/2 (half-angle) method.

(Water Contact Angle in State after Immersion in Methanol for 20 Minutes)

Each sample cut into a size of 50 mm×50 mm and having a PET film attached to the pressure-sensitive adhesive layer thereof was immersed in 100 mL methanol at room temperature (23° C.) for 20 minutes. Subsequently, the sample was pulled up from the methanol, and, prewashed by distilled water to remove methanol attached thereto. Then, the sample was air-dried at room temperature for 12 hours to prepare an evaluation sample.

The evaluation sample after being cut into a size of 10 mm×30 mm was fixed onto a glass plate by a double-faced adhesive tape, and set in the contact angle meter (Model: DROPMASTER-701, manufactured by Kyowa interface Science Co., Ltd.). A 2.0 μL droplet of distilled water was attached to the surface of the sample, and, after the elapse of 300 seconds since the start of the attachment, the contact angle (room temperature (23° C.) was measured by the measurement mode of the θ/2 (half-angle) method.

(Cross-Cut Stretching Test)

Each sample was cut into a size of 20 mm×70 mm, and a plurality of slits (11 slits extending in each of two orthogonal directions) were made by a cutter at intervals of 1 mm to extend at an angle of 45 degrees with respect to long sides of the sample, and have a depth at which only the antifouling layer is cut off, thereby forming a 10×10 lattice pattern. The lattice was formed in a central area of the sample. The sample was set in a tensile tester (AUTOGRAPH AGS-X, manufactured by Shimadzu Corporation), such that the slit area thereof was centrally located, at an inter-chuck distance of 50 mm, and stretched in a longitudinal direction at a stretching speed of 300 mm/min until the inter-chuck distance becomes 75 mm (stretching ratio: 1.5). After leaving the sample in the stretched state for 1 minute, the number of cells of the antifouling layer peeled off from the substrate layer was evaluated.

(Tensile Breaking Strength (after 60° C.×4 Days)

After attaching a separator (trade name "MRF38", manufactured by Mitsubishi Plastics, Inc., thickness: 38 μm) to the pressure-sensitive adhesive layer of each sample, the sample was immersed in pure water at 60° C. for 4 days. After pulling-up, water on the sample was wiped away, and the sample was left at room temperature (23° C.) for 1 hour. Then, the sample was cut into a size of 20 mm width×100 mm length. After peeling off the separator from the pressure-sensitive adhesive layer, the resulting sample was set in a tensile tester (AUTOGRAPH AGS-X, manufactured by Shimadzu Corporation) at an inter-chuck distance of 20 mm, and stretched at room temperature (23° C.) and at a stretching speed of 300 mm/min until the sample breaks, thereby evaluating a tensile breaking strength.

(Adhesive Force Test (after 60° C.×4 Days))

Each sample cut into a size of 20 mm width×80 mm length was laminated to (bright annealed (BA-)) SUS 304 at room temperature (23° C.) by one strike of a 2-kg roller. Then, after leaving the resulting laminate at room temperature (23° C.) for 12 hours, the laminate was stored in pure water at 60° C. for 4 days. After pulling-up, water on the laminate was wiped away, and the laminate was left at room temperature (23° C.) for 1 hour. Then, the sample was peeled off from the (BA-) SUS 304 at room temperature (23° C.) and at a peel angle of 180°. A force during the peeling was measured by using a tensile tester (AUTOGRAPH AGS-X, manufactured by Shimadzu Corporation), and defined as an adhesive force. With regard to Reference Example 8, as a result of this test, the pressure-sensitive adhesive layer was peeled off from the substrate layer, and remained on (BA-) SUS 304, so that it was "non-measureable". In this case, the adhesive force is infinity, and thus the ratio of the tensile breaking strength (N/20 mm)/the adhesive force (N/20 mm) is regarded as 0.

(Peelability)

Each sample cut into a size of 20 mm width×80 mm length was laminated to BA-) SUS 304 at room temperature (23° C.) by one strike of a 2-kg roller. Then, after leaving the resulting laminate at room temperature (23° C.) for 12 hours, the laminate was stored in pure water at 60° C. for 4 days. After pulling-up, water on the laminate was wiped away, and the laminate was left at room temperature (23° C.) for 1 hour. Then, the sample was peeled off from the SUS 304 at a peel angle of 145 to 180°, to evaluate whether the sample is broken during the peeling.

As shown in Table 2, it has been confirmed that the antifouling layer-including pressure-sensitive adhesive film can be peeled off without breaking, as long as the ratio of the ratio of the tensile breaking strength/the adhesive force is 1.5 or more. In each of Inventive Examples 1 to 18, the ratio of the tensile breaking strength/the adhesive force is 1.5 or more.

(Visible Light Transmittance)

Each sample cut into a size of 20 mm×20 mm was set in a measurement part of an integrating sphere unit (ISV-722, manufactured by JASCO Corporation) of an ultraviolet-visible spectrophotometer (V-660, manufactured by JASCO Corporation) to measure a transmittance in a wavelength range of 400 to 800 nm.

As a result of the measurement for Inventive Example 1, the transmittance was 91.5%, 92.8% and 93.1%, respectively, at 400 nm, 600 nm and 800 nm. Further, Inventive Examples 1, 7 and 8 were subjected to the measurement of the ultrasonic wave attenuation amount. As a result, the attenuation amounts thereof were, respectively, 2.7 db, 1.3 db, and 3.2 db, each of which was equivalent to or, equal to or less than that in the conventional measure.

Further, in order to confirm a relationship between antifouling capability against barnacles and the water contact angle, the following reference experiment was conducted.

Reference Experimental Example 1

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 32 weight parts of dimethyl silicone oil (trade name "KF96-100 cs", manufactured by Shin-Etsu Chemical Co. Ltd.), 18 weight parts of alkyl-modified silicone oil (trade name "KF415", manufactured by Shin-Etsu Chemical Co. Ltd.), and 5 weight parts of polyether-modified silicone oil (trade name "KF6016", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto the surface of an ionomer substrate (trade name "Himilan 1855", manufactured by Dupont-Mitsui Polychemicals Co., Ltd., thickness: 100 μm), using an applicator, and then cured at 140° C. for 2 minutes to obtain a 200 μm-thick, antifouling layer-attached substrate layer (antifouling layer (thickness: 100 μm)/substrate layer (thickness: 100 μm)).

<Production of Pressure-Sensitive Adhesive Layer>

A 50 μm-thick pressure-sensitive adhesive composition was obtained in the same manner as that in Inventive Example 1.

<Production of Antifouling Layer-Including Pressure-Sensitive Adhesive Film>

The pressure-sensitive adhesive layer obtained in Reference Example 1 was bonded to the substrate layer of the 200 μm-thick, antifouling layer-attached substrate layer (antifouling layer (thickness: 100 μm)/substrate layer (thickness: 100 μm)) obtained in Reference Example 1, using a laminator to obtain an antifouling layer-including pressure-sensitive adhesive film consisting of "antifouling layer (thickness: 100 μm)/substrate layer (thickness: 100 μm)/pressure-sensitive adhesive layer (thickness: 50 μm)).

Reference Experimental Example 2

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 13 weight parts of dimethyl silicone oil (trade name "KF96-100 cs", manufactured by Shin-Etsu Chemical Co. Ltd.), 7 weight parts of alkyl-modified silicone oil (trade name "KF415", manufactured by Shin-Etsu Chemical Co. Ltd.), and 5 weight parts of polyether-modified silicone oil (trade name "KF6016", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto the surface of an ionomer substrate (trade name "Himilan 1855", manufactured by Dupont-Mitsui Polychemicals Co., Ltd., thickness: 100 μm), using an applicator, and then cured at 140° C. for 2 minutes to obtain a 200 μm-thick, antifouling layer-attached substrate layer (antifouling layer (thickness: 100 μm)/substrate layer (thickness: 100 μm)).

<Production of Antifouling Layer-Including Pressure-Sensitive Adhesive Film>

The pressure-sensitive adhesive layer obtained in Reference Example 1 was bonded to the substrate layer of the 200 μm-thick, antifouling layer-attached substrate layer (antifouling layer (thickness: 100 μm)/substrate layer (thickness: 100 μm)) obtained in Reference Example 2, using a laminator to obtain an antifouling layer-including pressure-sensitive adhesive film consisting of "antifouling layer (thickness: 100 μm)/substrate layer (thickness: 100 μm)/pressure-sensitive adhesive layer (thickness: 50 μm)).

Reference Experimental Example 3

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 19 weight parts of dimethyl silicone oil (trade name "KF96-100 cs", manufactured by Shin-Etsu Chemical Co. Ltd.), 11 weight parts of alkyl-modified silicone oil (trade name "KF415", manufactured by Shin-Etsu Chemical Co. Ltd.), and 3 weight parts of polyether-modified silicone oil (trade name "KF6016", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto the surface of an ionomer substrate (trade name "Himilan 1855", manufactured by Dupont-Mitsui Polychemicals Co., Ltd., thickness: 100 μm), using an applicator, and then cured at 140° C. for 2 minutes to obtain a 200 μm-thick, antifouling layer-attached substrate layer (antifouling layer (thickness: 100 μm)/substrate layer (thickness: 100 μm)).

<Production of Antifouling Layer-Including Pressure-Sensitive Adhesive Film>

The pressure-sensitive adhesive layer obtained in Reference Example 1 was bonded to the substrate layer of the 200 μm-thick, antifouling layer-attached substrate layer (antifouling layer (thickness: 100 μm)/substrate layer (thickness: 100 μm)) obtained in Reference Example 3, using a laminator to obtain an antifouling layer-including pressure-sensitive adhesive film consisting of "antifouling layer (thickness: 100 μm)/substrate layer (thickness: 100 μm)/pressure-sensitive adhesive layer (thickness: 50 μm)).

Reference Experimental Example 4

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 26 weight parts of dimethyl silicone oil (trade name "KF96-100 cs", manufactured by Shin-Etsu Chemical Co. Ltd.), 15 weight parts of alkyl-modified silicone oil (trade name "KF415", manufactured by Shin-Etsu Chemical Co. Ltd.), and 1 weight part of polyether-modified silicone oil (trade name "KF6016", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto the surface of an ionomer substrate (trade name "Himilan 1855", manufactured by Dupont-Mitsui Polychemicals Co., Ltd., thickness: 100 μm), using an applicator, and then cured at 140° C. for 2 minutes to obtain a 200 μm-thick, antifouling layer-attached substrate layer (antifouling layer (thickness: 100 μm)/substrate layer (thickness: 100 μm)).

<Production of Antifouling Layer-Including Pressure-Sensitive Adhesive Film>

The pressure-sensitive adhesive layer obtained in Reference Example 1 was bonded to the substrate layer of the 200 μm-thick, antifouling layer-attached substrate layer (antifouling layer (thickness: 100 μm)/substrate layer (thickness: 100 μm)) obtained in Reference Example 4, using a laminator to obtain an antifouling layer-including pressure-sensitive adhesive film consisting of "antifouling layer (thickness: 100 μm)/substrate layer (thickness: 100 μm)/pressure-sensitive adhesive layer (thickness: 50 μm)).

Reference Experimental Example 5

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 19 weight parts of dimethyl silicone oil (trade name "KF96-100 cs", manufactured by Shin-Etsu Chemical Co. Ltd.), 11 weight parts of alkyl-modified silicone oil (trade name "KF415", manufactured by Shin-Etsu Chemical Co. Ltd.), and 1 weight part of polyether-modified silicone oil (trade name "KF6016", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto the surface of an ionomer substrate (trade name "Himilan 1855", manufactured by Dupont-Mitsui Polychemicals Co., Ltd., thickness: 100 μm), using an applicator, and then cured at 140° C. for 2 minutes to obtain a 200 μm-thick, antifouling layer-attached substrate layer (antifouling layer (thickness: 100 μm)/substrate layer (thickness: 100 μm)).

<Production of Antifouling Layer-Including Pressure-Sensitive Adhesive Film>

The pressure-sensitive adhesive layer obtained in Reference Example 1 was bonded to the substrate layer of the 200 μm-thick, antifouling layer-attached substrate layer (antifouling layer (thickness: 100 μm)/substrate layer (thickness: 100 μm)) obtained in Reference Example 5, using a laminator to obtain an antifouling layer-including pressure-sensitive adhesive film consisting of "antifouling layer (thickness: 100 μm)/substrate layer (thickness: 100 μm)/pressure-sensitive adhesive layer (thickness: 50 μm)).

Reference Experimental Example 6

<Production of Laminate of Antifouling Layer/Substrate Layer>

100 weight parts (agent A: 50 weight parts, agent B: 50 weight parts) of silicone resin (addition-type liquid silicone resin, trade name "KE-1935", manufactured by Shin-Etsu Chemical Co. Ltd.), 13 weight parts of dimethyl silicone oil (trade name "KF96-100 cs", manufactured by Shin-Etsu Chemical Co. Ltd.), 7 weight parts of alkyl-modified silicone oil (trade name "KF415", manufactured by Shin-Etsu Chemical Co. Ltd.), and 1 weight part of polyether-modified silicone oil (trade name "KF6016", manufactured by Shin-Etsu Chemical Co. Ltd.), were mixed together, and the resulting mixture was steered at room temperature (23° C.) for 5 minutes to obtain an antifouling layer-forming material liquid. The obtained antifouling layer-forming material liquid was applied onto the surface of an ionomer substrate (trade name "Himilan 1855", manufactured by Dupont-Mitsui Polychemicals Co., Ltd., thickness: 100 μm), using an applicator, and then cured at 140° C. for 2 minutes to obtain a 200 μm-thick, antifouling layer-attached substrate layer (antifouling layer (thickness: 100 μm)/substrate layer (thickness: 100 μm)).

<Production of Antifouling Layer-Including Pressure-Sensitive Adhesive Film>

The pressure-sensitive adhesive layer obtained in Reference Example 1 was bonded to the substrate layer of the 200 μm-thick, antifouling layer-attached substrate layer (antifouling layer (thickness: 100 μm)/substrate layer (thickness: 100 μm)) obtained in Reference Example 6, using a laminator to obtain an antifouling layer-including pressure-sensitive adhesive film consisting of "antifouling layer (thickness: 100 μm)/substrate layer (thickness: 100 μm)/pressure-sensitive adhesive layer (thickness: 50 μm)).

(Evaluation of Antifouling Capability)

Each evaluation sample was laminated to a polyvinyl chloride plate (trade name "KP plate", manufactured by Sumitomo Bakelite Co., Ltd.) having a size of 100 mm×150 mm, using a laminator, to obtain an antifouling property evaluation plate. The obtained antifouling property evaluation plate was immersed in the sea along the coast of Gamagori City of Aichi Prefecture at a water depth of 1 m, for 1 month. Then, the number of barnacles adhering to the surface of the antifouling layer-including pressure-sensitive adhesive film was visually evaluated.

A result of the evaluation is shown in Table 3

TABLE 3

| | Composition of Antifouling Layer (part) | | | | | Water Contact Angle (°) | |
| --- | --- | --- | --- | --- | --- | --- | --- |
| | KE-1935 | KF96-100cs | KF415 | KF6016 | Thickness (μm) | after Immersion in Methanol for 20 min | Number of barnacles (pieces/150 cm²) |
| Reference Experimental Example 1 | 100 | 32 | 18 | 5 | 100 | 38 | 0 |
| Reference Experimental Example 2 | 100 | 13 | 7 | 5 | 100 | 46 | 0 |
| Reference Experimental Example 3 | 100 | 19 | 11 | 3 | 100 | 59 | 0 |
| Reference Experimental Example 4 | 100 | 26 | 15 | 1 | 100 | 74 | 0 |
| Reference Experimental Example 5 | 100 | 19 | 11 | 1 | 100 | 89 | 18 |
| Reference Experimental Example 6 | 100 | 13 | 7 | 1 | 100 | 97 | 30 |

Figure 5:
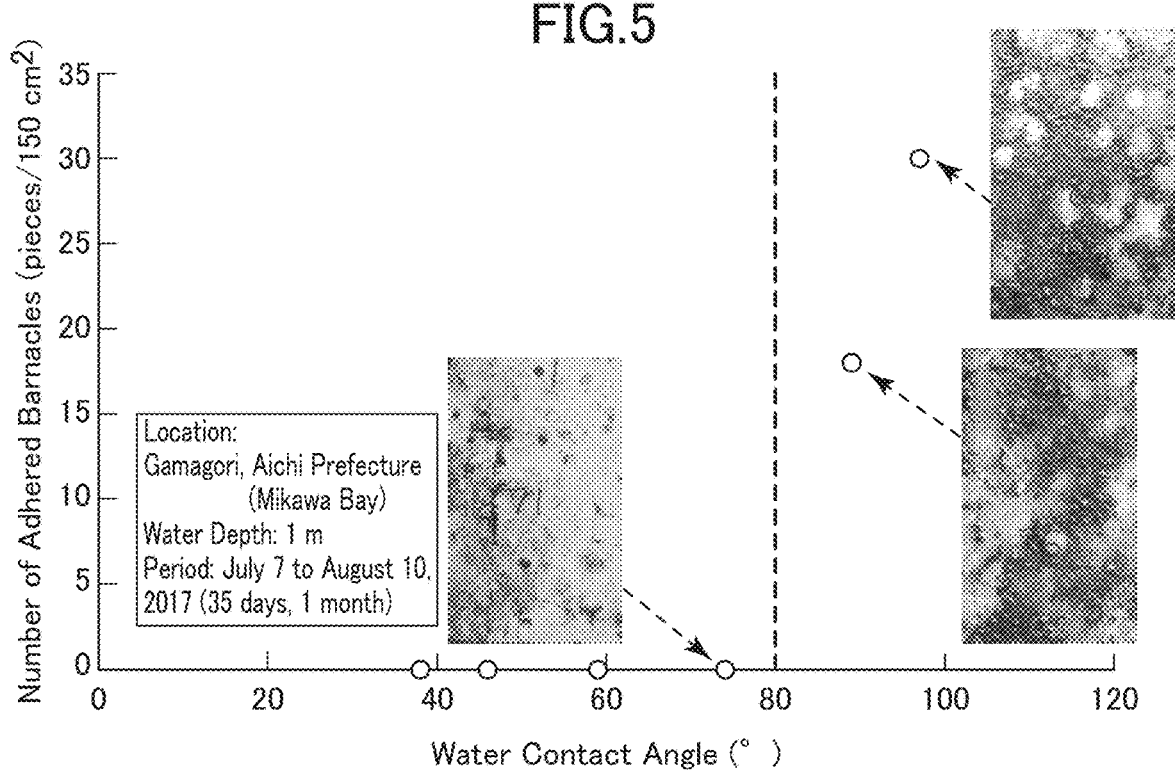
FIG. 5 is a graph showing a relationship between a water contact angle of an antifouling layer of the aquatic organism adherence preventive film and adherence of organisms.

FIG. 5 is a graph showing a relationship between the water contact angle of the antifouling layer of the aquatic organism adherence preventive film (antifouling layer-including pressure-sensitive adhesive film) and adherence of organisms. In a case where the water contact angle is used as an index for evaluating a hydrophilic property, it has been confirmed that aquatic organisms such as barnacles will not adhere as long as the water contact angle of the aquatic organism adherence preventive film is about 80 degrees or less. Thus, the point that the water contact angle of the aquatic organism adherence preventive film is about 80 degrees or less is one condition for preventing adherence of aquatic organisms.

Figure 6:
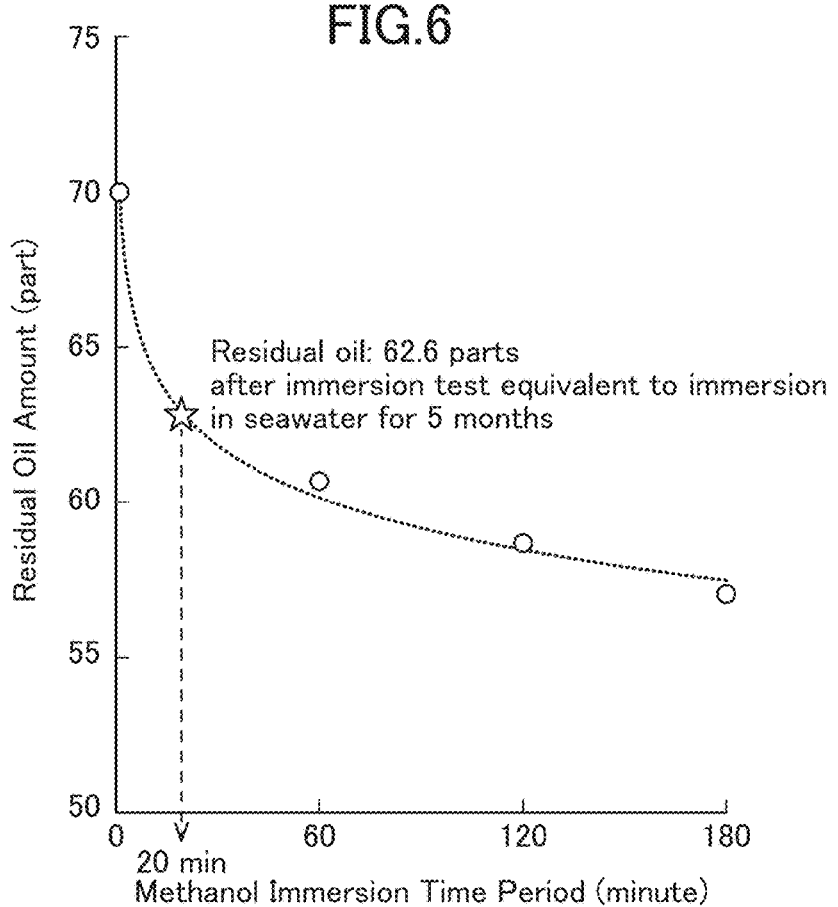
FIG. 6 is a graph showing a relationship between seawater immersion and methanol immersion of the antifouling layer of the aquatic organism adherence preventive film.

FIG. 6 is a graph showing a relationship between seawater immersion and methanol immersion of the antifouling layer of the aquatic organism adherence preventive film. When the aquatic organism adherence preventive film is immersed in seawater for a long period of time, the oil component is diffused from the antifouling layer toward the seawater. This diffusion from the antifouling layer toward the seawater can be promoted by means of methanol immersion, so that it is possible to substantially evaluate performance of the aquatic organism adherence preventive film within a short period of time. The amount of the oil component of the antifouling layer of the aquatic organism adherence preventive film being immersed in methanol was successively observed after elapsed of 0 min, 60 min, 120 min and 180 min, and each observed value was plotted on a graph with a circular mark to draw a curve. As a result, it has been confirmed that the oil component logarithmically decreases.

Further, a value (amount of the oil component: 62.6 parts) actually measured after immersing the aquatic organism adherence preventive film in seawater for 5 months was plotted on the curve (based on the circular marks) of the graph regarding the methanol immersion, with a star mark. As a result, it has been confirmed that the value corresponds to a methanol immersion time period of 20 minutes. Considering the above, as long as the water contact angle of the antifouling layer is 80 degrees or less at the time after immersion in seawater for 5 months, aquatic organisms such as barnacles will not adhere for one month since that time. Therefore, as long as the water contact angle of the antifouling layer after immersion in methanol for 20 minutes is 80 degrees or less, the antifouling layer has antifouling capability equivalent to that against immersion in seawater for 6 months.

As shown in Table 2, the water contact angle after immersion in methanol for 20 minutes (equivalent to immersion in seawater for 5 months) in each of Inventive Examples 1 to 18 is 80 degrees or less. Thus, it is confirmed that the aquatic organism adherence preventive film in each of Inventive Examples 1 to 18 has antifouling capability equivalent to that against immersion in seawater for 6 months. Assume that the aquatic organism adherence preventive film in each of Inventive Examples 1 to 18 is attached to the submersible sensor unit. In this case, at least within a use period of about six months, it is possible to almost completely prevent adherence of aquatic organisms by the antifouling layer on the surface of the aquatic organism adherence preventive film, and reduce the risk of failing to acquire data by the sensing function of the sensing part.

(Antifouling Performance of Antifouling Layer-Including Pressure-Sensitive Adhesive Film Containing Only Hydrophilic Oil)

Using laminate and film production methods similar to those for Inventive Examples and Reference Examples in Table 1, and a test method similar to that used for obtaining the antifouling layer-including pressure-sensitive adhesive film evaluation results shown in Tables 2 and 3, antifouling performance of an antifouling layer-including pressure-sensitive adhesive film containing only hydrophilic oil and exhibiting a water contact angle of 80 degrees or less was evaluated. A result of the evaluation is shown in Table 4. Reference Experimental Example 7 in Table 4 is an antifouling layer-including pressure-sensitive adhesive film produced in the same manner as that in Inventive Example 1, except that it contains silicone oil consisting only of hydrophilic oil, i.e., the ratio of hydrophobic oil (KF96-100 cs) to hydrophilic oil (KF6016) is set to 0 part/5 parts. Further, Reference Experimental Example 8 in Table 4 is shown for comparison with Reference Experimental Example 7, and is an antifouling layer-including pressure-sensitive adhesive film produced in the same manner as that in Inventive Example 1, except that the ratio of hydrophobic oil (KF96-100 cs) to hydrophilic oil (KF6016) is set to 55 parts/5 parts.

TABLE 4

| | Composition of Antifouling Layer (part) | | | | Thickness (μm) | Water Contact Angle (°) after Immersion in Methanol for 20 min | Number of barnacles (pieces/150 cm$^2$) |
|---|---|---|---|---|---|---|---|
| | KE-1935 | KF96-100cs | KF415 | KF6016 | | | |
| Reference Experimental Example 7 | 100 | 0 | 0 | 5 | 100 | 59.8 | 3 |
| Reference Experimental Example 8 | 100 | 55 | 0 | 5 | 100 | 50.1 | 0 |

The water contact angles after immersion in methanol for 20 min (equivalent to immersion in seawater for 5 months) in Reference Experimental Examples 7 and 8 are, respectively, 59.8 degrees and 50.1 degrees, each of which is equal to or less than about 80 degrees. Thus, it is confirmed that the antifouling layer-including pressure-sensitive adhesive film in each of Reference Experimental Examples 7 and 8 has antifouling capability equivalent to that against immersion in seawater for 6 months.

As a result of evaluating Reference Experimental Examples 7 and 8 by the antifouling capability evaluation method used for obtaining the evaluation result shown in Table 3, the number of barnacles per 150 cm$_2$ is 3 in Reference Experimental Example 7, and 0 in Reference Experimental Example 8. Thus, it has been confirmed that even an antifouling layer-including pressure-sensitive adhesive film containing only hydrophilic oil, as in Reference Experimental Example 7, provides sufficient antifouling performance.

From the above evaluation results, when an aquatic organism adherence preventive film equivalent to that in Reference Experimental Example 7 is attached to an underwater structure, an antifouling layer on the surface of the aquatic organism adherence preventive film can almost completely prevent adherence of aquatic organisms to the underwater structure, at least within a use period of six months.

(Evaluation of Adhesion Performance of Antifouling Layer-Including Pressure-Sensitive Adhesive Film)

Each sample of plural types of aquatic organism adherence preventive films (antifouling layer-including pressure-sensitive adhesive films) produced by variously changing the addition amount (weight part(s)) of each of hydrophobic oil and hydrophilic oil such as polyether-modified silicone oil to be contained in the aquatic organism adherence preventive film (antifouling layer-including pressure-sensitive adhesive film) according the present invention (see, e.g., Table 1) was stretched at a stretch ratio of 1.5 to 4 by a cross-cut stretching test used for obtaining the result shown in Table 2, to evaluate adhesion performance of each of the aquatic organism adherence preventive films during stretching. In the cross-cut stretching test conducted with respect to Inventive and Reference Examples shown in Table 1, the antifouling layer-including pressure-sensitive adhesive film is stretched at a stretch ratio of 1.5 and observes the number of cells of the antifouling layer peeled off from the substrate layer of the film, as seen in the result shown in Table 2. Further, from a viewpoint of adhesion between the film substrate and the antifouling layer in the antifouling layer-including pressure-sensitive adhesive film, a combination ratio between hydrophilic oil and hydrophobic oil for allowing the antifouling layer to become less likely to be peeled off from a substrate layer even at a higher stretch ratio was confirmed. Basically, in the evaluation of adhesion performance, laminate and film production methods similar to those for Inventive Examples and Reference Examples in Table 1, and a test method similar to that used for obtaining the antifouling layer-including pressure-sensitive adhesive film evaluation results shown in Tables 2 and 3 were used.

A result of the evaluation of adhesion performance of each antifouling layer-including pressure-sensitive adhesive film during stretching is shown in Table 5 to 7. Tables 5 to 7 show: a combination ratio between the addition amount (weight part(s)) of hydrophilic silicone oil, and the addition amount (weight part(s)) of hydrophobic silicone oil, in each sample of the antifouling layer-including pressure-sensitive adhesive films; and a stretch ratio at the time when the antifouling layer is peeled off from the substrate layer in the sample during stretching of the sample by the cross-cut stretching test.

TABLE 5

| Sample No. | Addition Amount (weight part(s)) of Hydrophilic Silicone Oil (Total amount of KF6013, KF6015, KF6016 and KF6017) | Addition Amount (weight part(s)) of Hydrophobic Silicone Oil (Total amount of KF100cs, KF415, and KF50-100cs | | | | | | Silicone Oil (weight part(s)) *: Contact angle NG | | Water Contact Angle (°) after Immersion in Methanol for 20 min |
|---|---|---|---|---|---|---|---|---|---|---|
| | | 1.5 @ Stretch ratio at peel-off | 2.0 @ Stretch ratio at peel-off | 2.5 @ Stretch ratio at peel-off | 3.0 @ Stretch ratio at peel-off | 3.5 @ Stretch ratio at peel-off | 4 @ Stretch Ratio at peel-off | Hydrophilic | Hydrophobic | |
| T27 | 20 | 60.0 | | | | | | 20 | 60.0 | 36 |
| T28 | 13 | | 66.7 | | | | | 13 | 66.7 | 37 |
| T29 | 11 | | | 69.3 | | | | 11 | 69.3 | 38 |
| T30 | 7 | | | | 73.3 | | | 7 | 73.3 | 41 |
| T31 | 4 | | | | | 76.0 | | 4 | 76.0 | 48 |
| T17 | 15 | 45.0 | | | | | | 15 | 45.0 | 39 |
| T18 | 10 | | 50.0 | | | | | 10 | 50.0 | 42 |
| T19 | 8 | | | 52.0 | | | | 8 | 52.0 | 42 |
| T20 | 5 | | | | 55.0 | | | 5 | 55.0 | 46 |
| T21 | 3 | | | | | | 57.0 | 3 | 57.0 | 58 |
| T22 | 10 | | 30.0 | | | | | 10 | 30.0 | 40 |

TABLE 5-continued

| Sample No. | Addition Amount (weight part(s)) of Hydrophilic Silicone Oil (Total amount of KF6013, KF6015, KF6016 and KF6017) | Addition Amount (weight part(s)) of Hydrophobic Silicone Oil (Total amount of KF100cs, KF415, and KF50-100cs | | | | | | Silicone Oil (weight part(s)) *: Contact angle NG | | Water Contact Angle (°) after Immersion in Methanol for 20 min |
|---|---|---|---|---|---|---|---|---|---|---|
| | | 1.5 @ Stretch ratio at peel-off | 2.0 @ Stretch ratio at peel-off | 2.5 @ Stretch ratio at peel-off | 3.0 @ Stretch ratio at peel-off | 3.5 @ Stretch ratio at peel-off | 4 @ Stretch Ratio at peel-off | Hydrophilic | Hydrophobic | |
| T23 | 7 | | 33.3 | | | | | 7 | 33.3 | 42 |
| T24 | 5 | | | 34.7 | | | | 5 | 34.7 | 44 |
| T25 | 3 | | | | 36.7 | | | 3 | 36.7 | 54 |
| T26 | 2 | | | | 38.0 | | | 2 | 38.0 | 65 |
| KRT45 | 15 | | 55 | | | | | 15 | 55 | 36 |
| KRT65 | 10 | | | 60 | | | | 10 | 60 | 40 |
| KRT84 | 20 | 8.3 | | | | | | 20 | 8.3 | 41 |
| KRT98 | 3 | | | | | 67 | | 3 | 67 | 66 |
| KRT100 | 6 | | | | | 64 | | 6 | 64 | 44 |
| KRT101 | 7 | | | | 63 | | | 7 | 63 | 43 |
| KRT102 | 8 | | 62 | | | | | 8 | 62 | 40 |

TABLE 6

| Sample No. | Addition Amount (weight part(s)) of Hydrophilic Silicone Oil (Total amount of KF6013, KF6015, KF6016 and KF6017) | Addition Amount (weight part(s)) of Hydrophobic Silicone Oil (Total amount of KF100cs, KF415, and KF50-100cs | | | | | | Silicone Oil (weight part(s)) *: Contact angle NG | | Water Contact Angle (°) after Immersion in Methanol for 20 min |
|---|---|---|---|---|---|---|---|---|---|---|
| | | 1.5 @ Stretch ratio at peel-off | 2.0 @ Stretch ratio at peel-off | 2.5 @ Stretch ratio at peel-off | 3.0 @ Stretch ratio at peel-off | 3.5 @ Stretch ratio at peel-off | 4 @ Stretch Ratio at peel-off | Hydrophilic | Hydrophobic | |
| Inventive Example 1 | 15 | | 55 | | | | | 15 | 55 | 50.1 |
| Inventive Example 2 | 10 | | 65 | | | | | 10 | 65 | 56 |
| Inventive Example 3 | 10 | | 60 | | | | | 10 | 60 | 57 |
| Inventive Example 4 | 10 | | 60 | | | | | 10 | 60 | 67.5 |
| Inventive Example 5 | 5 | | | | 65 | | | 5 | 65 | 58.2 |
| Inventive Example 6 | 6 | | 43 | | | | | 6 | 43 | 69.5 |
| Inventive Example 7 | 15 | | 55 | | | | | 15 | 55 | 48.2 |
| Inventive Example 8 | 15 | | 55 | | | | | 15 | 55 | 47.8 |
| Inventive Example 9 | 15 | | 55 | | | | | 15 | 55 | 48.4 |
| Inventive Example 10 | 15 | | 55 | | | | | 15 | 55 | 49.7 |
| Inventive Example 11 | 15 | | 55 | | | | | 15 | 55 | 48.5 |
| Inventive Example 12 | 15 | | 55 | | | | | 15 | 55 | 49.6 |
| Inventive Example 13 | 15 | | 55 | | | | | 15 | 55 | 49 |
| Inventive Example 14 | 15 | | 55 | | | | | 15 | 55 | 51.2 |
| Inventive Example 15 | 15 | | 55 | | | | | 15 | 55 | 52.8 |
| Inventive Example 16 | 15 | | 55 | | | | | 15 | 55 | 49.3 |
| Inventive Example 17 | 15 | | 55 | | | | | 15 | 55 | 50.6 |
| Inventive Example 18 | 5 | | | | 65 | | | 5 | 65 | 55.2 |
| Reference Example 1 | 0 | | | | 70 | | | 0* | 70* | 103.2 |
| Reference Example 2 | 1 | | 45.5 | | | | | 1* | 45.5* | 91.3 |

TABLE 6-continued

| Sample No. | Addition Amount (weight part(s)) of Hydrophilic Silicone Oil (Total amount of KF6013, KF6015, KF6016 and KF6017) | Addition Amount (weight part(s)) of Hydrophobic Silicone Oil (Total amount of KF100cs, KF415, and KF50-100cs | | | | | | Silicone Oil (weight part(s)) *: Contact angle NG | | Water Contact Angle (°) after Immersion in Methanol for 20 min |
|---|---|---|---|---|---|---|---|---|---|---|
| | | 1.5 @ Stretch ratio at peel-off | 2.0 @ Stretch ratio at peel-off | 2.5 @ Stretch ratio at peel-off | 3.0 @ Stretch ratio at peel-off | 3.5 @ Stretch ratio at peel-off | 4 @ Stretch Ratio at peel-off | Hydrophilic | Hydrophobic | |
| Reference Example 3 | 15 | 55 | | | | | | 15 | 55 | 49.4 |
| Reference Example 4 | 15 | | 55 | | | | | 15 | 55 | 49.7 |
| Reference Example 5 | 0 | | | | 10 | | | 0* | 10* | 96.6 |
| Reference Example 6 | 30 | 60 | | | | | | 30 | 60 | 56.7 |
| Reference Example 7 | 5 | | 75 | | | | | 5* | 75* | 82.7 |
| Reference Example 8 | 20 | | 70 | | | | | 20 | 70 | 62.7 |

TABLE 7

| Sample No. | Addition Amount (weight part(s)) of Hydrophilic Silicone Oil (Total amount of KF6013, KF6015, KF6016 and KF6017) | Addition Amount (weight part(s)) of Hydrophobic Silicone Oil (Total amount of KF100 cs, KF415, and KF50-100cs | | | | | | Silicone Oil (weight part(s)) *: Contact angle NG | | Water Contact Angle (°) after Immersion in Methanol for 20 min |
|---|---|---|---|---|---|---|---|---|---|---|
| | | 1.5 @ Stretch ratio at peel-off | 2.0 @ Stretch ratio at peel-off | 2.5 @ Stretch ratio at peel-off | 3.0 @ Stretch ratio at peel-off | 3.5 @ Stretch ratio at peel-off | 4 @ Stretch Ratio at peel-off | Hydrophilic | Hydrophobic | |
| KRT51 | 6 | | | 43 | | | | 6 | 43 | 70 |
| KRT99 | 4 | | | | | 66 | | 4 | 66 | 55 |
| KRT85 | 20 | 3.2 | | | | | | 20 | 3.2 | 52 |
| KRT133 | 10 | 0 | | | | | | 10 | 0 | 41 |
| KRT132 | 5 | | 0 | | | | | 5 | 0 | 60 |
| KRT66 | 20 | | 50 | | | | | 20 | 50 | 53 |
| KRT117 | 5 | | | | 25 | | | 5 | 25 | 68 |
| KRT118 | 5 | | | 15 | | | | 5 | 15 | 64 |
| KRT119 | 3 | | | | | 25 | | 3* | 25* | 86 |
| KRT120 | 3 | | | | 15 | | | 3* | 15* | 93 |
| KRT44 | 15 | | 55.0 | | | | | 15 | 55.0 | 57 |
| KRT134 | 5 | | | | | 150 | | 5 | 150 | 54 |
| KRT135 | 20 | | | | 150 | | | 20 | 150 | 40 |
| KRT136 | 20 | | | | 120 | | | 20 | 120 | 41 |
| KRT137 | 20 | | | 100 | | | | 20 | 100 | 42 |
| KRT138 | 20 | | | 80 | | | | 20 | 80 | 41 |
| KRT139 | 30 | | | | 150 | | | 30 | 150 | 39 |
| KRT140 | 30 | | | | 120 | | | 30 | 120 | 40 |
| KRT141 | 40 | | | | 150 | | | 40 | 150 | 39 |
| KRT95 | 30 | 40 | | | | | | 30 | 40 | 50 |
| KRT96 | 40 | 30 | | | | | | 40 | 30 | 45 |
| KRT97 | 50 | 20 | | | | | | 50 | 20 | 43 |

For example, in the antifouling layer-including pressure-sensitive adhesive film of the sample No. "T27" (Table 5), the addition amounts (weight parts) of hydrophilic silicone oil and hydrophobic silicone oil are, respectively, "20" and "60", and the stretch ratio at peel-off of the antifouling layer from the substrate layer of the film (hereinafter referred to as "stretch ratio at peel-off") is "2.0". Further, in the antifouling layer-including pressure-sensitive adhesive film of the sample No. "KRT51" (Table 7), the addition amounts (weight parts) of hydrophilic silicone oil and hydrophobic silicone oil are, respectively, "6" and "43", and the stretch ratio at peel-off of the antifouling layer from the substrate layer of the film (hereinafter referred to as "stretch ratio at peel-off") is "2.5". The samples of the antifouling layer-including pressure-sensitive adhesive films shown in Table 6 are the same films in Inventive Examples 1 to 18 and Reference Examples 1 to 8 shown in Table 1. In the column "Silicone Oil (weight part(s))" on the right side of each of Tables 5 to 7, the addition amounts (weight parts) of hydrophilic silicone oil and hydrophobic silicone oil are described side-by-side, merely for the sake of organizing.

FIG. 7 is a plot diagram showing a relationship between the combination ratio between hydrophilic silicone oil and hydrophobic silicone oil, and the stretch ratio at peel-off of the antifouling layer, shown in Tables 5 to 7. On a plot diagram in which the X axis (horizontal axis) represents the addition amount (weight part(s)) of hydrophilic silicone oil (expressed as "Hydrophilic Silicone (part)"), and the Y axis (vertical axis) represents the addition amount (weight part(s)) of hydrophobic silicone oil (expressed as "Hydrophobic Silicone (part)"), six kinds of points each denoting a respective one of the samples having stretching ratios at peel-off of 1.5 to 4 are plotted. As the evaluation result of the adhesion performance of the antifouling layer-including pressure-sensitive adhesive film, it is confirmed that the sample falling within a region surrounded by the broken line (broken line region) described on the plot diagram shown in FIG. 7 has a stretching ratio at peel-off of 2.5 or more, i.e., is a desirable antifouling layer-including pressure-sensitive adhesive film.

The broken line on the X-Y coordinate is expressed as the following formulas of straight lines: y=−5.6x+43.6; x=6; y=3.3x+14.3; y=21x+17; and y=−x+90, and the broken line region is a region surrounded by the 5 straight lines. The following discussion will be made by dividing the broken line region of the plot diagram in FIG. 7 into a triangular area and the remaining area. Firstly, discussing the triangular area in the broken line region, from a viewpoint of adhesion between the substrate layer and the antifouling layer of the film, among the samples of the antifouling layer-including pressure-sensitive adhesive films, a desirable one having a stretching ratio at peel-off of 2.5 or more falls within a region in which x is from 1 to 6 (1<x<6), and y is from (−5.6x+43.6) to 38 ((−5.6x+43.6)<y<38), where x denotes the addition amount (weight part(s)) of hydrophilic silicone oil, and y denotes the addition amount (weight part(s)) of hydrophobic silicone oil.

Secondly, discussing the area other than triangular area, from a viewpoint of adhesion between the substrate layer and the antifouling layer of the film, among the samples of the antifouling layer-including pressure-sensitive adhesive films, a desirable one having a stretching ratio at peel-off of 2.5 or more falls within a region in which y is from (3.3x+14.3) to (21x+17) ((3.3x+14.3)<y<(21x+17)), and y is from 34 to (−x+90) (34<y<(−x+90)), where x denotes the addition amount (weight part(s)) of hydrophilic silicone oil, and y denotes the addition amount (weight part(s)) of hydrophobic silicone oil. However, in the sample (Reference Example 7) whose mark falls within the broken line region and is encircled by a circle, although the addition amount (weight part(s)) x of hydrophilic silicone oil is 5, and the addition amount (weight part(s)) y of hydrophobic silicone oil is 75, as assigned with the mark * in the column "Silicone Oil (weight part(s))" in Tables 5 to 7, the water contact angle is 80 degrees or more. Therefore, this sample is excluded from the broken line region. Further, in the samples (Reference Examples 1, 2 and 5, KRT119 and KRT120) each located outside the broken line region and encircled by a circle, the water contact angle is also 80 degrees or more. Further, in the sample (Reference Example 2) whose mark falls within the broken line region and is encircled by a broken line circle, although the addition amount (weight part(s)) x of hydrophilic silicone oil is 10, and the addition amount (weight part(s)) y of hydrophobic silicone oil is 65, the stretch ratio at peel-off is 2. Therefore, this sample is excluded from the broken line region indicating that the stretch ratio at peel-off is 2.5 or more. It is considered that this sample (Reference Example 2) fails to obtain a stretch ratio at peel-off of greater than 2, because it contains long-chain alkyl-modified silicone oil, wherein this silicone oil is contained more than other oil by a certain rate.

From the above evaluation result of the adhesion performance of each antifouling layer-including pressure-sensitive adhesive film (Tables 5 to 7), it is possible to set a desired region of the combination ratio between hydrophilic oil and hydrophobic oil of antifouling layer-including pressure-sensitive adhesive film in view of the adhesion.

INDUSTRIAL APPLICABILITY

As mentioned above, the present invention can be advantageously used for preventing adhesion of aquatic organisms to a sensing part of a submersible sensor unit such as an ADCP.

LIST OF REFERENCE SIGNS

100: aquatic organism adherence preventive film
110: antifouling layer
120: substrate layer
130: pressure-sensitive adhesive layer
140: release liner
150: protective film
200: submersible sensor unit (multi-layer flow direction/velocity meter)
210: sensor (ultrasonic transmitting part)
212: mounting member

The invention claimed is:

1. A submersible sensor unit comprising:
a housing having at least one sensing opening;
a sensor disposed inside the housing such that a sensing face thereof faces the sensing opening of the housing; and
an aquatic organism adherence preventive film attached to the housing or the sensing face such that it closes up the sensing opening of the housing, wherein the aquatic organism adherence preventive film has transmissibility with respect to at least one of light and a sonic wave,
wherein the aquatic organism adherence preventive film is a laminate comprising: a substrate layer; a pressure-sensitive adhesive layer bonded to one surface of the substrate layer; and an antifouling layer bonded to the substrate layer on a side opposite to the pressure-sensitive adhesive layer,
wherein the antifouling layer has a water contact angle of 80 degrees or less, as measured after 5 minutes have elapsed since operation of causing the antifouling layer to be in contact with methanol for 20 minutes, and then dropping water on the antifouling layer,
wherein the antifouling layer contains silicone resin and silicone oil, and
wherein the silicone oil contains hydrophobic silicone oil and hydrophilic silicone oil.

2. The submersible sensor unit as recited in claim 1, wherein a ratio of a tensile breaking strength (N/20 mm) as measured after immersion in pure water at 60° C. for 4 days to an adhesive force (N/20 mm) with respect to the submersible sensor unit, as measured after immersion in pure water at 60° C. for 4 days, is 1.5 or more.

3. The submersible sensor unit as recited in claim 1, wherein a 1-mm square cross-cut stretching-caused peeling degree of the antifouling layer with respect to the substrate layer is 0.30 or less.

4. The submersible sensor unit as recited in claim 1, wherein an amount of attenuation of a 1 MHz ultrasonic wave due to the aquatic organism adherence preventive film is 5.0 db or less.

5. The submersible sensor unit as recited in claim 1, wherein the aquatic organism adherence preventive film has a transmittance in a wavelength range of 400 to 800 nm of 80% or more.

6. The submersible sensor unit as recited in claim 1, wherein the antifouling layer has a thickness of 10 μm to 1000 μm.

7. The submersible sensor unit as recited in claim 1, wherein the substrate layer comprises a polyethylene-based ionomer substrate.

8. The submersible sensor unit as recited in claim 1, wherein the substrate layer has a thickness of 10 μm to 1000 μm.

9. The submersible sensor unit as recited in claim 1, wherein the pressure-sensitive adhesive layer has a thickness of 1 μm to 1000 μm.

* * * * *